US011324541B2

(12) United States Patent
Eggers

(10) Patent No.: US 11,324,541 B2
(45) Date of Patent: May 10, 2022

(54) THERMAL INCISION APPARATUS, SYSTEM AND METHOD

(71) Applicant: Eggers & Associates, LLC, Dublin, OH (US)

(72) Inventor: Philip E. Eggers, Dublin, OH (US)

(73) Assignee: Eggers & Associates, LLC, Dublin, OH (US)

( * ) Notice: Subject to any disclaimer, the term of this patent is extended or adjusted under 35 U.S.C. 154(b) by 615 days.

(21) Appl. No.: 16/141,253

(22) Filed: Sep. 25, 2018

(65) Prior Publication Data

US 2019/0099210 A1    Apr. 4, 2019

Related U.S. Application Data

(60) Provisional application No. 62/566,565, filed on Oct. 2, 2017.

(51) Int. Cl.
*A61B 18/10*    (2006.01)
*A61B 18/08*    (2006.01)
(Continued)

(52) U.S. Cl.
CPC ............ *A61B 18/10* (2013.01); *A61B 18/082* (2013.01); *A61B 18/14* (2013.01);
(Continued)

(58) Field of Classification Search
CPC ... A61B 2018/10; A61B 18/082; A61B 18/14; A61B 2018/1412; A61B 2018/00089;
(Continued)

(56) References Cited

U.S. PATENT DOCUMENTS

| 5,082,804 A | * | 1/1992 | Prabhu | ...................... C03C 8/04 |
| | | | | 428/209 |
| 5,254,115 A | * | 10/1993 | Bhatta | ................ A61B 17/3211 |
| | | | | 606/16 |

(Continued)

FOREIGN PATENT DOCUMENTS

CA        2403346 A1     9/2001

OTHER PUBLICATIONS

Precision Ceramics; Aluminum nitride (ALN): Ceramic materials. (May 1, 2017). Retrieved Apr. 23, 2021, from https://precision-ceramics.com/materials/aluminum-nitride/ (Year: 2017).*

(Continued)

*Primary Examiner* — Daniel W Fowler
*Assistant Examiner* — Annie L Patton
(74) *Attorney, Agent, or Firm* — Mueller Law, LLC; Jerry K. Mueller, Jr.

(57) ABSTRACT

Thermal cutting surgical instruments incorporate a blade incorporating a first substrate of high thermal conductivity material in the heated portion of the blade and a support and, the first substrate of high thermal conductivity material joined to a second substrate of low thermal conductivity material in the support region of the blade; an electrically insulative dielectric layer disposed on the first surface of the first substrate and on the first surface of second substrate; an electrically resistive heating element disposed on the electrically insulative dielectric; electrically conductive power leads and electrically conductive sense leads disposed on the electrically insulative dielectric layer and that are in electrical communication with the electrically resistive heating element; and an electrically insulative dielectric overcoat layer disposed on the electrically resistive heating element and on the distal portion of the electrically conductive power leads and electrically conductive sense leads.

29 Claims, 12 Drawing Sheets

(51) Int. Cl.
*A61B 18/14* (2006.01)
*A61B 18/00* (2006.01)

(52) U.S. Cl.
CPC .............. *A61B 2018/00089* (2013.01); *A61B 2018/00095* (2013.01); *A61B 2018/00101* (2013.01); *A61B 2018/00428* (2013.01); *A61B 2018/00601* (2013.01); *A61B 2018/00714* (2013.01); *A61B 2018/00875* (2013.01); *A61B 2018/1412* (2013.01)

(58) Field of Classification Search
CPC ........... A61B 2018/00101; A61B 2018/00714; A61B 2018/00095; A61B 2018/000875
See application file for complete search history.

(56) References Cited

U.S. PATENT DOCUMENTS

| | | | | |
|---|---|---|---|---|
| 5,308,311 | A * | 5/1994 | Eggers | A61B 17/3211 600/28 |
| 5,911,719 | A * | 6/1999 | Eggers | A61B 18/082 606/31 |
| 9,526,566 | B1 * | 12/2016 | Johnson | A61B 18/1445 |
| 9,549,774 | B2 * | 1/2017 | Denis | A61B 18/04 |
| 2016/0242836 | A1 * | 8/2016 | Eggers | A61B 18/149 |

OTHER PUBLICATIONS

Engineers Edge, L. (Jun. 6, 2017). Thermal properties of metals, conductivity, thermal expansion, specific heat: Engineers edge. Retrieved Apr. 23, 2021, from https://www.engineersedge.com/properties_of_metals.htm (Year: 2017).*

Belavic, D., Hrovat, M., Hole, J., Zarnik, M. S., Kosec, M., & Pavlin, M. (2007). The application of thick-film technology in c-mems. Journal of Electroceramics, 19(4), 363-368. doi:10.1007/s10832-007-9064-z (Year: 2007).*

Kasap, S. O., Capper, P. (Aug. 2017). Springer Handbook of electronic and Photonic Materials. Springer. (Year: 2017).*

* cited by examiner

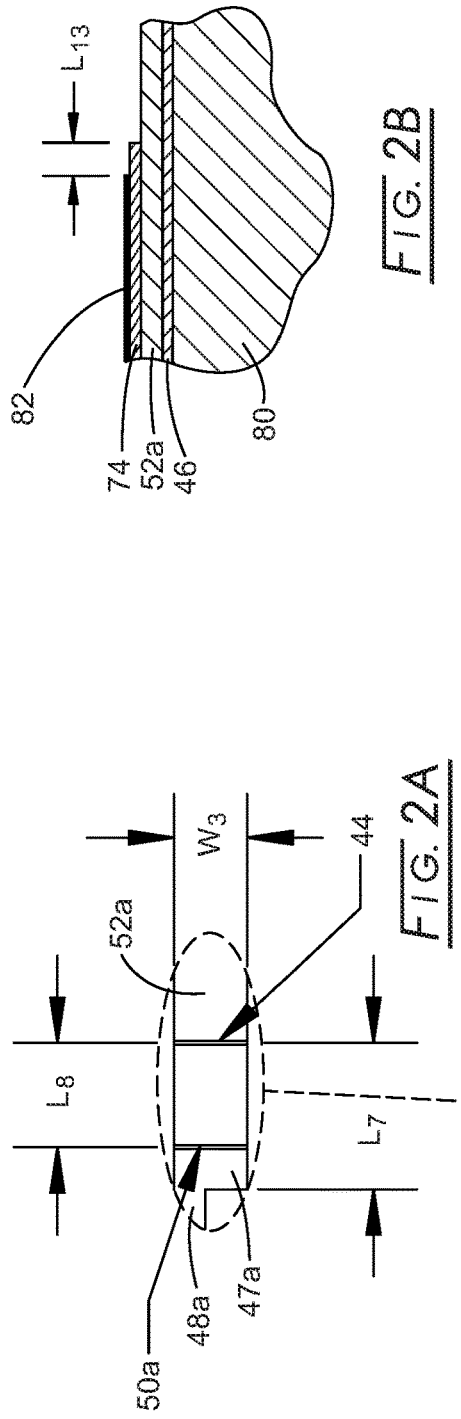
FIG. 2A
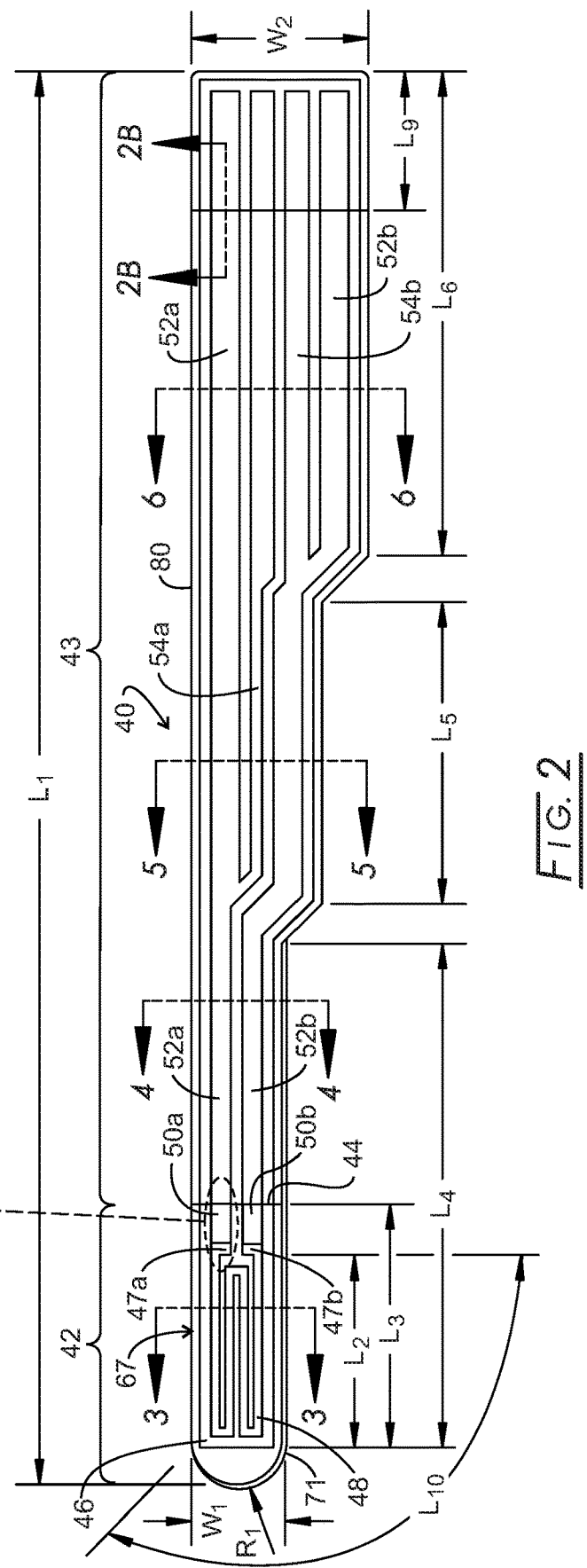
FIG. 2B
FIG. 2

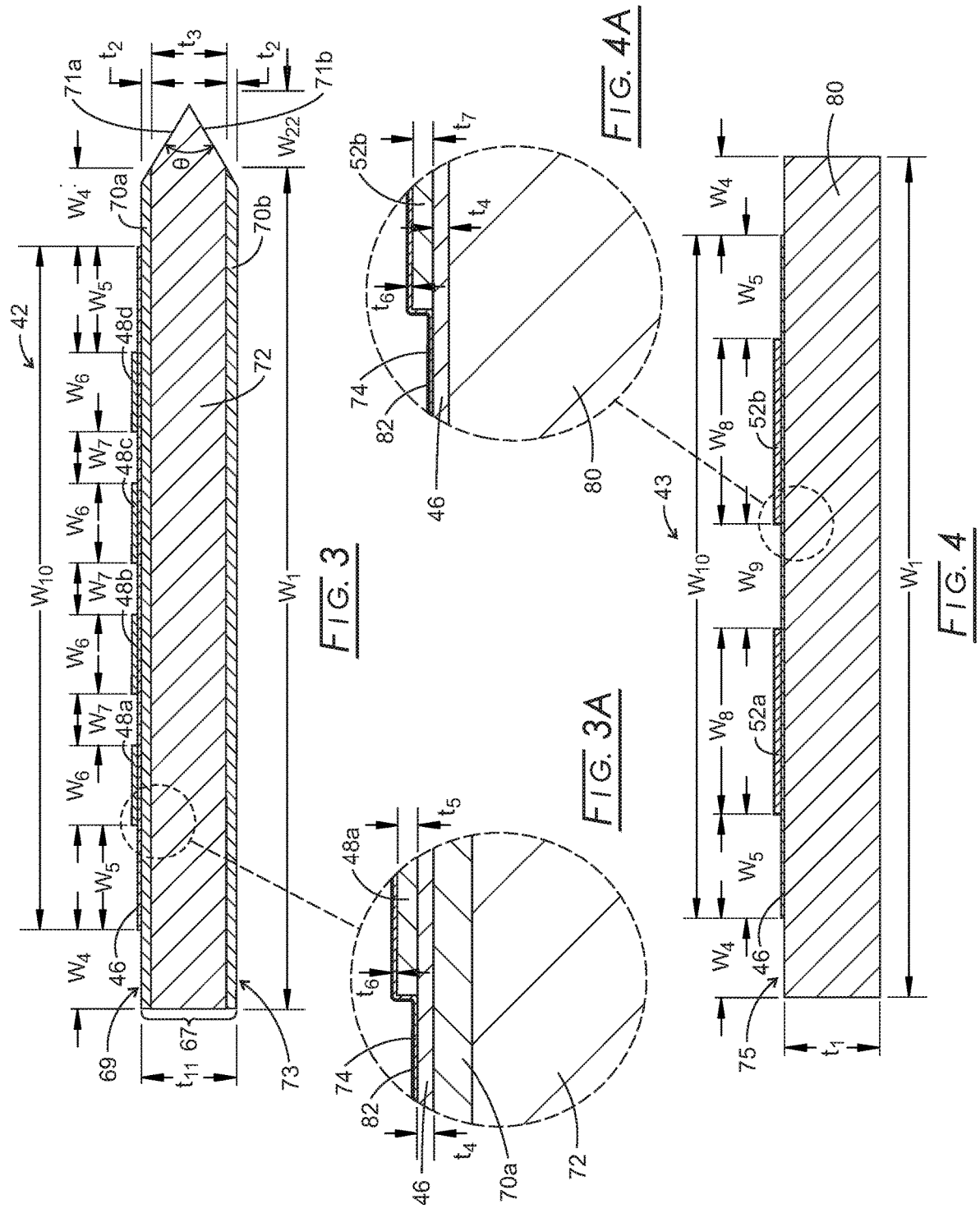

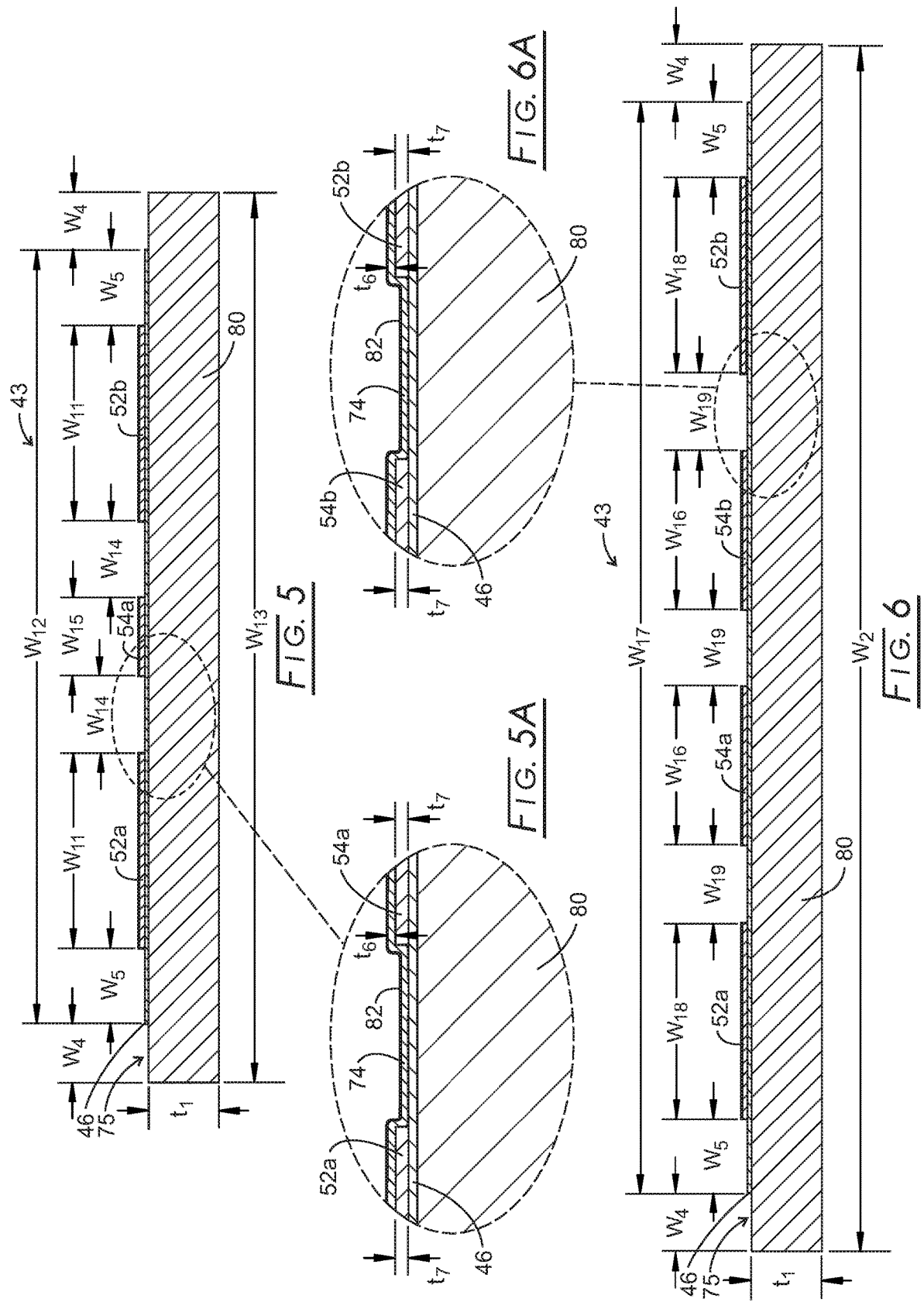

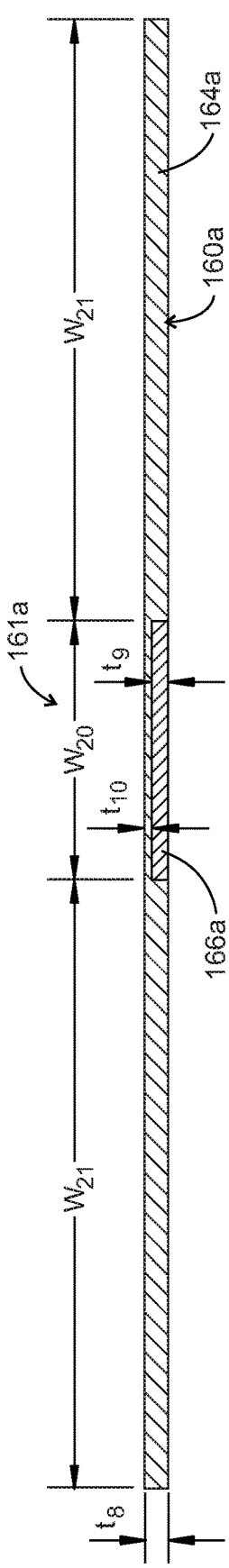
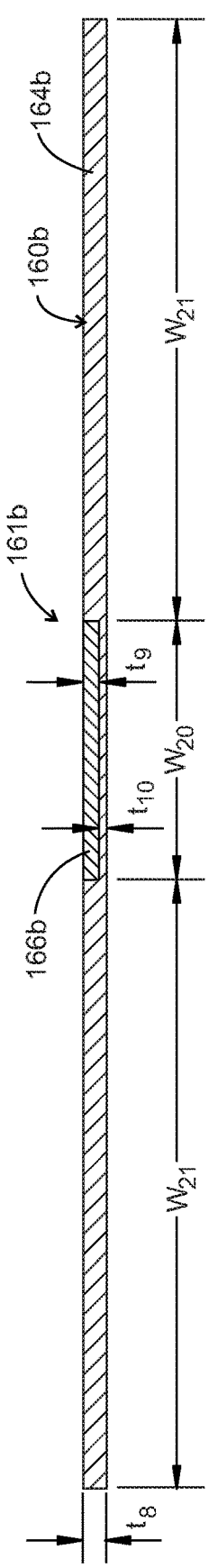
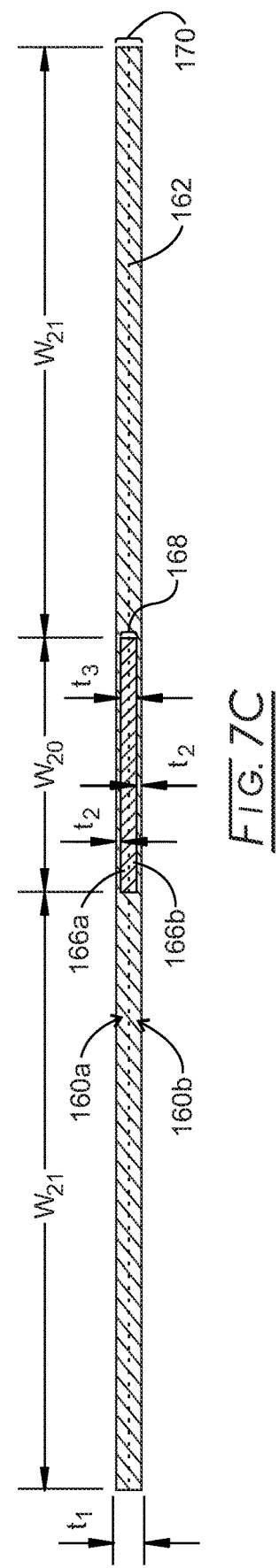
FIG. 7A
FIG. 7B
FIG. 7C

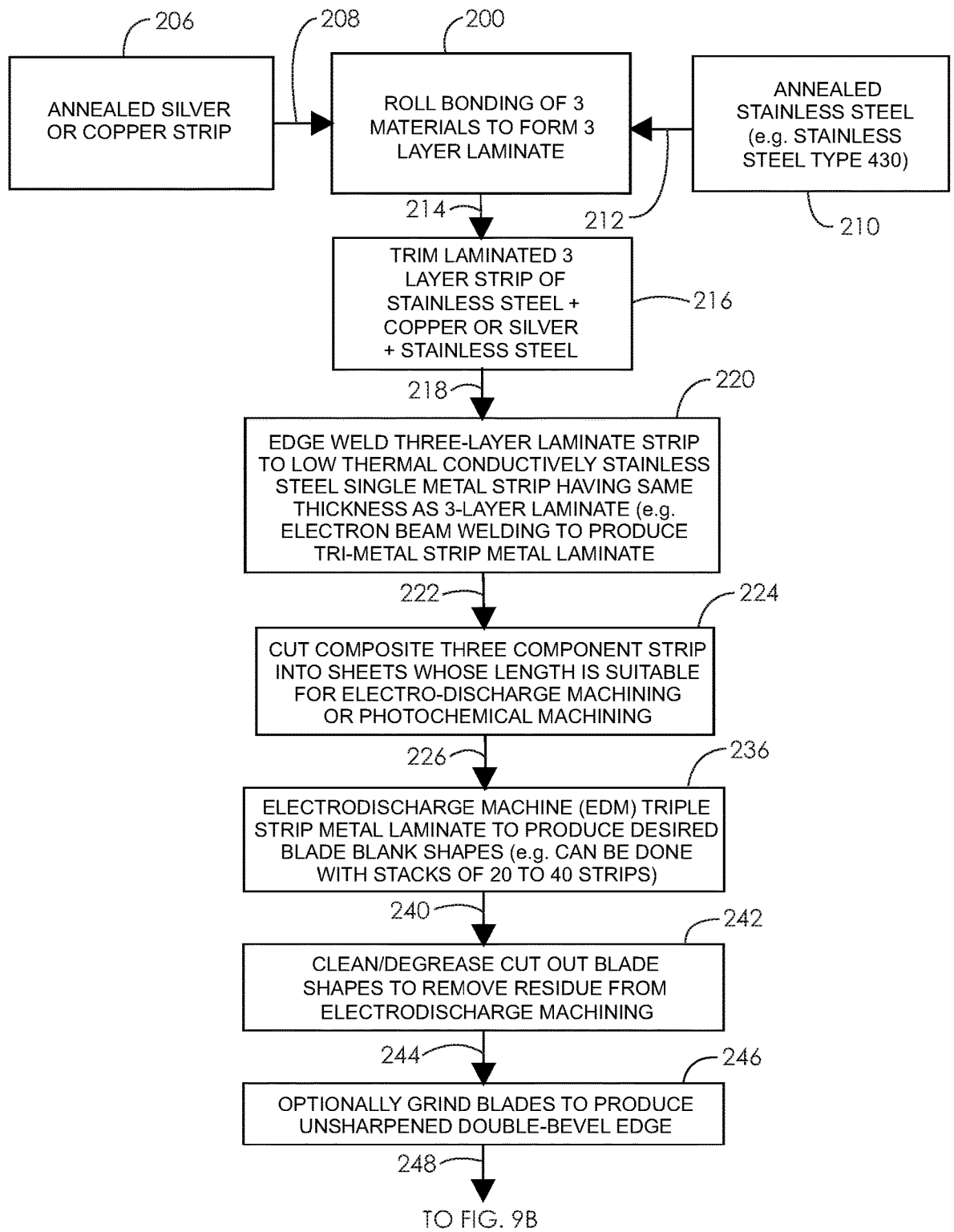

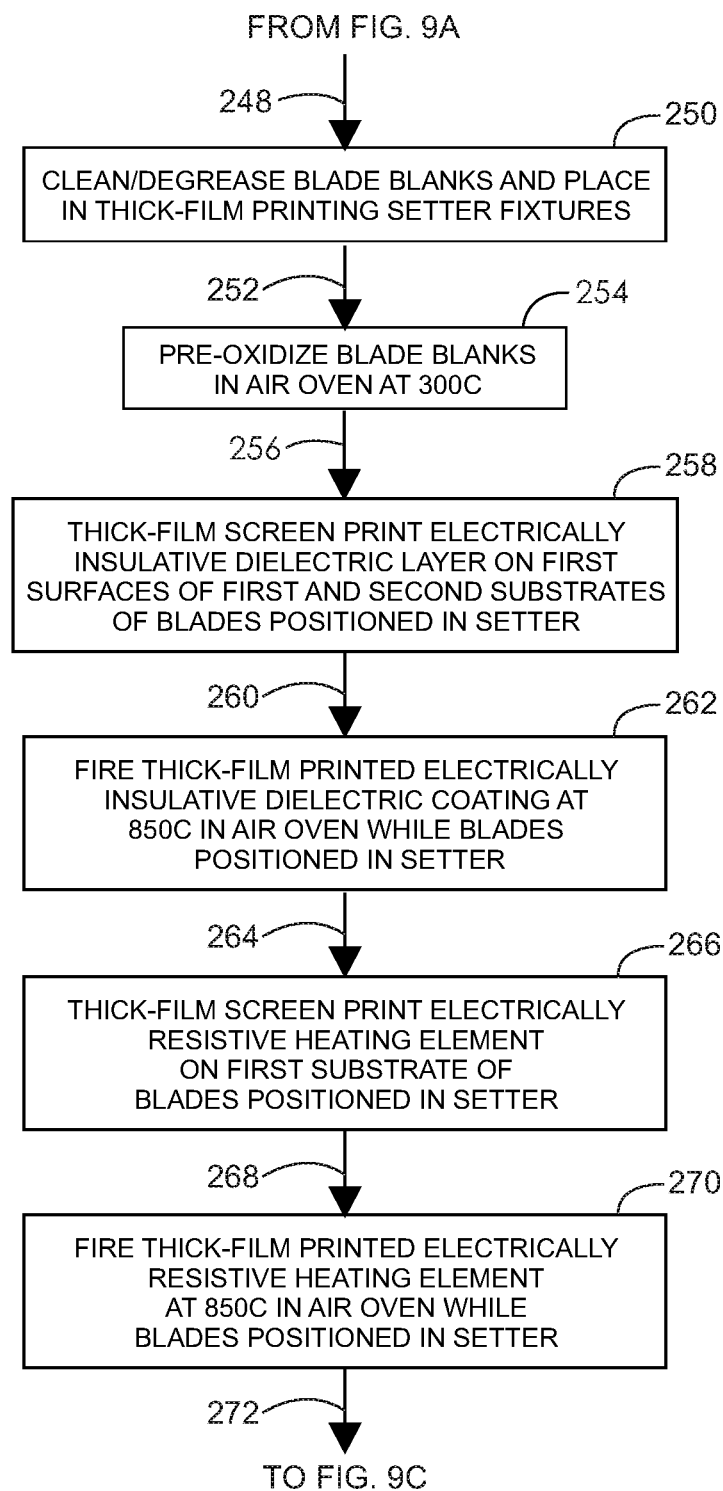

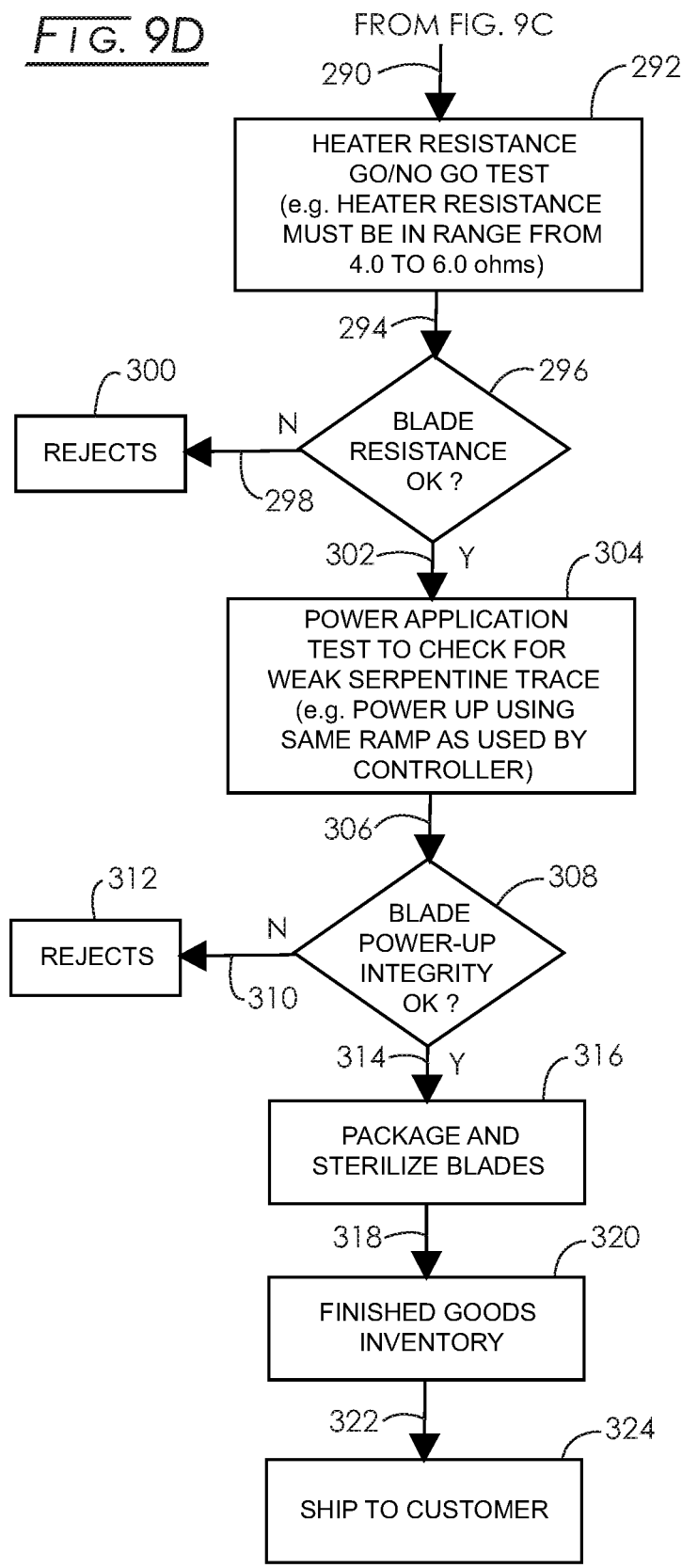

THERMAL INCISION APPARATUS, SYSTEM AND METHOD

CROSS-REFERENCE TO RELATED APPLICATIONS

This application claims benefit of provisional application 62/566,565 filed Oct. 2, 2017.

STATEMENT REGARDING FEDERALLY SPONSORED RESEARCH

Not applicable.

BACKGROUND

The control of bleeding during surgery accounts for a major portion of the time involved in an operation. In particular, bleeding that occurs when tissue is incised obscures the surgeon's vision, delays the operation, and reduces the precision of cutting. In addition, blood loss from the patient during surgery must be minimized to reduce or eliminate the need for supplementary blood transfusions.

Conventional surgical procedures are carried out utilizing a sequence of surgical instruments or tools. At the outset of a given procedure, sharp mechanical devices, such as a scalpel, are employed to part the skin layers so as to provide external access to the body cavity. Bleeding during such initial stages may be controlled through the use of ties, clamps, blotting procedures, and the like. As the body cavity is accessed, tissue not only is cut but also is manipulated to the extent that blunt counterparts often supplant mechanically sharp instruments.

These blunt counterparts electrically perform cutting and blood coagulating functions on demand and require the passage of high frequency electrical current through the tissue being cut and/or coagulated. Such technology, known as monopolar electrosurgery, has been available to surgeons for decades. For instance, a physicist, William T. Bovie, first developed a monopolar electrosurgical device over sixty years ago. This early device is described, for example, in U.S. Pat. No. 1,813,902, issued Jul. 14, 1931, entitled "Electrosurgical Apparatus", has met with acceptance over the years within the surgical community to the extent that current versions are referred to as the "Bovie". Such devices typically consist of a handle having a first or "active" electrode extending from one end. The other end of the handle is electrically coupled, via a cable, to an electrosurgical generator that provides a high frequency electric current in either a continuous high-frequency alternative current cutting mode or a pulsed coagulating mode. A remote control switch is attached to the generator and commonly is present in the form of a switch on the handle and/or as a foot switch located in proximity to the operating theater. During an operation, a second or "return" electrode, having a much larger surface area than the active electrode, will be positioned in contact with the skin of the patient. To remove tissue, the surgeon brings the active electrode into proximity with the tissue to be cut or coagulated. This is a starting condition where the instrument has not touched tissue. At this point in time, an electrical switch is actuated whereupon the active electrode is brought into close proximity with the tissue to be cut or coagulated. Electrical current then arcs from the active electrode to the adjacent tissue and flows through deeper tissue to reach the larger return electrode. In a cutting mode, the electrical arcing and corresponding current flow results in a highly intense, but localized heating, which causes cell destruction and tissue severance. Following a short cutting routine, the instrument again is elevated in still air away from the tissue for two or three seconds. In general, the device can be switched to a pulsed, higher voltage input to perform in a coagulating mode wherein a shower of arcs impinge on the adjacent tissue to effect the sealing of smaller transected blood vessels. The cutting and coagulation effect depends on the formation of small arcs between the active electrode and the adjacent tissue requiring that a small air gap be maintained to support the formation of essential electrical arcs. Disadvantageously, the application of tamponade by pressing the surgical instrument against the tissue containing the transected vessel(s) to temporarily interrupt the flow of blood from vessels (e.g., vessels having a lumen size greater than about 1 mm) is not possible since such applied pressure would prevent the essential arc formation.

Another common modality for electrosurgery is referred to as bipolar electrosurgery. With this approach, no large return electrode is in contact with the patient. Instead, a bipolar electrosurgical instrument is made having first and second electrodes arranged in close mutual proximity. The device is utilized with a dedicated bipolar cable that is inserted in appropriate bipolar outlets of an electrosurgical generator, a device found essentially in all major health care facilities. When switch activated, the bipolar device provides an electrical current that is conducted through intervening tissue located between a first electrode and a second electrode. Tissue disposed between the electrodes is heated by the flow of electrical current and the intervening tissue is coagulated. However, the current intensity is generally insufficient to enable the cutting of tissue and no electrical arcs are formed as in the case of the monopolar electrosurgery modality described above. In general, surgeons are trained in the use of both bipolar and monopolar modalities; however, particularly in conjunction with endoscopic applications, bipolar devices are becoming more accepted in view of safety considerations. In the latter regard, the bipolar approach overcomes certain of the more undesirable characteristics of monopolar instruments in that excessive necrosis is reduced and current is not passed extensively through the body of the patient. Since current arcs between adjacent electrodes, blood vessels are readily cauterized. Bipolar devices, however, generally require other auxiliary means for cutting the tissue being coagulated.

Typically, the ubiquitous electrosurgical generators exhibit outputs with frequencies ranging from about 350 KHz to 1 MHz. Such higher radiofrequency frequencies serve to avoid tissue stimulation that would otherwise occur at lower frequencies.

Investigators also have considered the implementation of resistive heating to carry out coagulation and cutting in surgery. One of the early devices known as an electrocautery device employed a very fine wire formed as a loop or extending linearly between spaced mounting points. Formed, for example, of platinum, the thinness or small diameter of the heated wire was required in order to gain a high enough resistance to develop correspondingly high enough temperature levels in conjunction with practical current levels. The requisite thinness of the wire resulted in marginal strength or rigidity, thus restricting applications of such instruments to spot coagulation with the application of a minimum level of pressure to the targeted vessel.

Surgical blades have been developed with mechanically sharp edges and side mounted electrical heating elements. With these instruments, cutting is achieved at the mechanically sharp facet edge of the blade and the coagulation or hemostasis is intended to develop as a result of contact of the sides of the blade and blade facets with the cut tissue. This, unfortunately, represents an attempt to stop bleeding after cutting, as opposed to a more desirable procedure for simultaneous cutting with coagulation. Prior art devices have employed resistance feedback control to maintain the heater temperature at a substantially constant user selected temperature under conditions ranging from operation in air (requiring minimum power deliver to heating element) to direct contact with vascular tissue (requiring maximum power delivery to heating element). In such prior art devices, the user selects the desired blade operating temperature in the range from about 70 C to 300 C. In surgical use with the blade in contact with tissue, the temperature at the cutting edge and adjacent blade facets is lower than the user selected operating temperature due to thermal impedances in the pathway between the heating element and the cutting edge and adjacent blade facets. In addition, to minimize adherence of blood coagulum and tissue during surgical use, it is essential that the lateral surfaces and facets of the blade that contact tissue are coated with a non-stick coating, such as polytetrafluoroethylene. Such non-stick coating unavoidably introduces an additional thermal impedance between the heated cutting blade and the tissue owing to the very low thermal conductivity of available non-stick coating materials. In this regard, see U.S. Pat. Nos. 4,481,057, 4,485,810, 5,308,311, 8,142,425 and 8,475,444.

Unlike monopolar electrosurgical instruments that cut tissue with electrical arcs that form between a blunt edge of the monopolar electrode "blade" and the adjacent tissue being cut or coagulated, prior art resistively heated devices have also been described that employ blunt cutting portions (i.e., unsharpened edges) that provide both thermally induced incision as well as coagulation without the passage of electrical current through the tissue being cut and/or coagulated. Thermal incision or "cutting" of tissue is achieved by transferring a sufficient heat flux to the tissue via the conduction heat transfer mode to induce rapid vaporization of cellular water within the tissue. The rapid vaporization of the cellular water that comprises up to 70% of all tissue further induces fragmentation of the cells with the result of weakening the tissue structure and consequent breaking apart of tissue in a manner that has the effect of tissue "cutting". Such prior art resistively heated devices utilize a defined thermal cutting portion emulating surgical blades and other implements, often with edge facets having an included angle ranging from about 20 to 40 degrees. The minimum temperature required to induce the thermal cutting of tissue has been previously determined to be about 400 to 500 C. Equally important, at tissue contacting blade surface temperatures above about 400 C, tissue and blood coagulum does not adhere thereby eliminating the need for the use of a non-stick coating and the need for removal of tissue and coagulum debris from the tissue contacting portions of the blade. In this regard, one of the first such devices for the thermal cutting of tissue with a resistively heated blunt blade is seen in Eggers' U.S. Pat. No. 5,591,719 issued Jun. 15, 1999, entitled "Resistively Heating Cutting and Coagulating Surgical Instrument".

Some resistively heated devices achieve a thermally induced cutting effect wherein the heating method employs a self-regulating temperature characteristic. Self-regulating (also known as auto-regulating) resistively heated devices maintain the cutting surface of the surgical device within a pre-selected elevated temperature range. An approach for attaining self-regulation has been to employ a ferromagnetic material in constructing the tissue-contacting end (i.e., the heating element) of the surgical instrument. When radiofrequency current is passed through a ferromagnetic material, the current density is concentrated near its outer surface. This current density attenuates exponentially as the distance into the material from the surface increases, a phenomenon known as the "skin effect".

The depth of the skin effect, i.e., the distance of penetrating current density into the ferromagnetic material, is defined as the depth at which current is reduced to approximately 37% of its surface value. This depth may be expressed mathematically as follows:

$$\text{Skin Depth}, d = C \times \sqrt{[\rho/(\mu^* f)]} \quad \text{(Equation 1)}$$

where d is the skin depth measured in centimeters, $\rho$ is the electrical resistivity in ohm-centimeters, $\mu$ is electrical relative magnetic permeability of the ferromagnetic material, C is a constant, viz. 503, and f is frequency of the applied alternating electrical potential in Hertz.

In ferromagnetic materials, such as iron, nickel, cobalt, and respective alloys, adjacent atoms and molecules couple their magnetic moments together in rigid parallelism (an interaction known as exchange coupling) in spite of the randomizing tendency of the thermal motion of atoms. If the temperature of such material is raised above a "Curie" temperature, specific for each ferromagnetic material composition, the noted exchange coupling suddenly disappears. As a result, these materials exhibit large changes in relative permeability as the temperature of the ferromagnetic material transitions to its Curie temperature. As seen from equation (1), since the relative permeability is known to change in response to the temperature of the material, the associated skin depth also will change. This relationship between skin depth and temperature enables ferromagnetic material based instruments to achieve temperature auto-regulation.

The heating elements of surgical devices have been constructed incorporating a ferromagnetic material that is selected to have a Curie temperature at or near the auto-regulation temperature desired for a particular surgical application. As a radiofrequency current passes through the ferromagnetic material, the heating element will resistively heat to approximately the Curie temperature. Once the cutting edge contacts tissue, both it and the area surrounding it will cool to a level below the Curie temperature. In response to this Curie transition, the skin depth will decrease which, in turn, results in an increased resistance of the cooled region (the resistance being a function of the ferromagnetic material's electrical resistivity multiplied by the current flow path length and divided by the current flow path area). A corresponding increase in the level of power supplied will accompany this increase in resistance. The temperature will then tend to again increase due to the increased level of resistive heating with the heating element increasing toward the Curie temperature. Thus, auto-regulation of the surgical component around the Curie temperature is achieved. See, for example, Eggers U.S. Pat. No. 5,480,398, issued Jan. 2, 1996, entitled "Endoscopic Instrument with Disposable Auto-Regulating Heater"; and Eggers, et al., U.S. Pat. No. 5,480,397, issued Jan. 2, 1996, entitled "Surgical Instrument with Auto-Regulating Heater and Method of Using Same".

Other radiofrequency powered, resistively heated surgical devices achieve a thermally induced cutting effect wherein the heating element comprises a thin coating of ferromagnetic material deposited on a non-ferromagnetic metal substrate, such as, a round or flat hairpin-shaped loop of metal. The thickness of the ferromagnetic coating is on the order of the several skin depths, as specified above in Equation 1. In this ferromagnetic heating element design, the ferromagnetic material and operating frequency is selected such that, in those distal portions of the hairpin loop coated with the ferromagnetic material, the electrical current predominantly flows within the electrically resistive ferromagnetic coating and only minimally within the non-ferromagnetic blade substrate that exhibits a relative low electrical impedance with respect to current flow. In those proximal regions of the hairpin loop not coated with a ferromagnetic material, the electrical current flows though the non-ferromagnetic support portions of the hairpin loop. The Curie temperature of the selected ferromagnetic material coating serves to establish a maximum upper temperature limit during surgical use and the selected level of constant current determines the operating temperature range of the tissue-contacting blade (e.g., ferromagnetic material coated Beryllium-Copper hairpin-type blade) as a function of the tissue effect being attempted (e.g., tissue cutting, tissue ablation, tissue desiccation). In this regard, see U.S. Pat. Nos. 8,292,879, 8,419, 724, 9,549,774, and U.S. Publication Number US 2015/0327907.

A disadvantage associated with prior art resistively heated thermal cutting devices that employ a ferromagnetic blade substrate or ferromagnetic coatings on a non-ferromagnetic hairpin-shaped round or flat wire substrate, is concerned with a lack of sufficient localization of heat at the blunt thermal cutting edge. In this regard, the entire heating element, including the support for its thermal cutting edge, is heated to a temperature of at least 400 to 500 C required to effect thermal cutting of tissue. In addition, the temperature of the ferromagnetic heating element can increase to as high as the Curie temperature of the ferromagnetic heating element (e.g., 600 to 700 C). Such elevated temperatures poses a risk that the support portions of the heating element that are proximal to those portions intended for tissue contact and cutting may contact tissue or organs not selected for incision causing unwanted thermal injury to the tissue or organs. Additionally, the time period required for the ferromagnetic heating element disposed in the cutting region to cool down to safe levels posing no threat of thermal injury can be quite significant. This time period, for example, may be ten seconds or more, an interval, which in a surgical environment is considered excessive, several seconds or less being considered acceptable, a starting condition interval to which surgeons are accustomed.

Another disadvantage associated with prior art resistively heated thermal cutting devices that employ a ferromagnetic blade substrate or a ferromagnetic coating on a non-ferromagnetic substrate is the operating temperature of the blade can extend over a wide range from the minimum allowed temperature for thermal cutting of tissue (viz., 400 to 500 C) to the Curie temperature of the ferromagnetic material, which can be as high as 600 to 700 C. In practice, the skin depth of a ferromagnetic material actually increases only gradually as the ferromagnetic heating element approaches the Curie temperature. As a consequence, maintaining the temperature of a ferromagnetic heating element above the minimum temperature of 500 C to ensure effective thermal cutting under all heat dissipation conditions in tissue requires a Curie temperature that is at least about 100 C greater than the minimum desired temperature. Conditions during surgery that can significantly affect the rate of heat dissipation include the vascularity of tissue, the rate of advancement of cutting blade through tissue and the length of the blade in contact with tissue. This wide operating temperature range of the ferromagnetic heating element above the minimum required thermal cutting temperature of 500 C produces smoke that obscures visibility and necessitates the use of auxiliary smoke evacuation apparatus and methods, further complicating the surgical procedure.

Another disadvantage associated with prior art ferromagnetic resistively heated devices for thermal cutting of tissue is concerned with the requirement that they must be powered by a specially designed or dedicated radiofrequency power supply operating at frequencies ranging from about 300 kHz to over 20 MHz. These dedicated power supply systems generally are configured to be unique to the properties of a particular heating element and are not of a universal nature, such that they would be usable with different surgical implements. In order to maximize the auto-regulation effect, the energy source used to apply power to the heating element preferably operates at a substantially constant current.

Yet another disadvantage of some prior art ferromagnetic resistively heated devices for thermal cutting of tissue is concerned with their inability to apply tamponade with the heated blade member to [a] interrupt the flow of blood long enough to allow the heated blade to effect the sealing of the transected blood vessels or [b] apply heat to pre-seal larger blood vessels before they are transected.

As a consequence of the foregoing considerations, practitioners have found it necessary to provide device-dedicated radiofrequency energy sources for powering thermal cutting surgical devices as well as auxiliary smoke evacuation systems. Of course, such added equipment requirements pose budgetary concerns to health care institutions.

BRIEF SUMMARY

The present invention is addressed to surgical instruments employing the thermal cutting of tissue. As used herein, the thermal cutting of tissue refers to the severing of tissue by means of heating the blade and the tissue contacting surface of a surgical instrument to a sufficiently high temperature of at least 400 to 500 C to thermally weaken the tissue structure to the point that division of the tissue can be accomplished with an otherwise blunt, unsharpened edge. The mechanism of "cutting" employed in the thermal cutting of tissue is distinct from that of a conventional scalpel wherein a surgically sharp cutting edge is employed to mechanically sever and divide tissue without the need for elevating the temperature of the cutting edge.

In contrast to radiofrequency-powered devices for the thermal cutting of tissue incorporating heating elements based on the skin effect, an effect which concentrates electrical current flow in a confined depth of a ferromagnetic conductor or coating on a non-ferromagnetic conductor operating below its Curie temperature, the instruments now presented are heated by a resistive heating element disposed on a dielectric coating bonded to a blunt blade member. The level of heating power generated in heating elements based on ferromagnetic materials depends on both the temperature-dependent skin depth and the applied current level resulting in heating element temperatures that can vary over a broad range of 100 C or more. This broad range of temperature variation is dependent on the conditions during surgery that affect the rate of heat dissipation, the conditions including the vascularity of tissue, the rate of advancement of cutting blade through tissue and the length of the blade in contact with tissue.

Unlike thermal cutting surgical devices that incorporate ferromagnetic heating elements, the thermal cutting surgical instruments now presented utilize resistance-feedback control to regulate the temperature of the heating element to within about 5 C of the optimum temperature for the thermal cutting of tissue (e.g., an optimum preselected temperature of 500 C). The resistance-feedback control of the heating element, wherein the heating element is disposed on an electrically insulative dielectric layer interposed between the heating element and the blade substrate, enables a nearly constant heating element temperature to be maintained over the entire range of possible heat dissipation conditions. Such heat dissipation conditions range from operation of the heated blade in still air to exposure of the full length of the heated portion of the blade to highly vascular tissue during passage through the tissue at the maximum rate of advancement.

The thermal cutting surgical instruments of the present disclosure incorporate a blade comprising two distinct portions, a distal portion constituting a heated portion of the blade and a proximal portion constituting a support member portion of the blade. The heated portion of blade includes a substrate having relatively high thermal conductance in order to minimize thermal gradients across the length or the width of the heated portion of the blade. Such gradients can otherwise exist when the only a small portion of the entire heated length of the blade is in contact with tissue with the resulting heat dissipation that occurs at the blade/tissue interface limited to only a small fraction of the length of the heater.

By way of example, a first substrate supporting the resistance heater in the heated portion of the blade may be a high thermal conductivity material, such as, for example, silver, silver alloy, copper or a copper alloy. By way of another example, the substrate supporting the resistance heater in the heated portion of the blade may comprise a laminate structure produced by conventional roll bonding of dissimilar metals comprising a core of copper or silver surrounded on either side by stainless steel claddings on both sides of the copper or silver core (e.g., stainless steel Type 430 or 304). Such a three-layer laminate increases the stiffness of the heated portion of the blade by the buttressing effect of the stainless steel owing to its much higher modulus of elasticity than that of the high thermal conductivity copper or silver core material. The stainless steel claddings of equal thickness on either side of a copper or silver or silver core also serve to limit warpage due to any difference in the thermal expansion coefficient of the copper or silver core and stainless steel cladding materials. In addition, the stainless steel cladding disposed on the copper or silver core enables an improved level of chemical bonding between the electrically insulative dielectric layer and the stainless steel cladding present in the heated portion of the blade. Preferably, the high thermal conductivity metal selected for first substrate or core of first substrate is greater than 2 watt/cm-C, more preferably greater than 3 watt/cm-C.

The use of a known biocompatible material, such as silver, in the core of the three layer laminate structure is advantageous since a biocompatible coating is not required over the exposed edge portions of the first substrate involving a copper core. A biocompatible coating will otherwise be required since copper is known to be cytotoxic with respect to human cells and, therefore, can not be used in contact with human tissue or blood during surgical procedures. In this regard, see Cortizo, M., et al., Cytotoxicity of Copper Ions Released from Metal. Biological Trace Elements Research, December 2004; 102(1-3); 129-141. The biocompatible coatings may include materials such as, for example, titanium nitride, titanium aluminum nitride, chromium nitride, zirconium nitride, gold, silver and, if the maximum operating temperature is below 500 C, Parylene HT® (Parylene HT® being a registered trademark of Specialty Coating Systems, Inc., Indianapolis Ind.).

The support member portion of the blade incorporates a substrate having a relatively low thermal conductance in order to minimize heat conduction from the heated portion of the blade through the support member portion of the blade and into the handpiece that supports the blade. By way of example, a second substrate comprising the support member portion of the blade may be a low thermal conductivity material such as stainless steel Type 304 or 430. Preferably, the thermal conductivity of metal selected for support member portion of blade is less than 0.6 watt/cm-C, more preferably less than 0.3 watt/cm-C.

The first substrate exhibiting high thermal conductance in the heated portion of the blade having a first thickness is joined by a welding process to a second substrate exhibiting low thermal conductance in a support member portion of the blade having a second thickness. The first and second substrates may advantageously have equal first and second thicknesses so that a composite of the two substrates is planar and having a uniform thickness. The composite of the first and second substrates having a uniform thickness enables subsequent thick-film printing processes including the printing and firing of one or more electrically insulative dielectric layers on the upper surfaces of the first and second substrates including the weld zone located at the boundary between the first and second substrates.

Alternatively, a slot may be formed in a strip (e.g., by grinding) of stainless steel substrate material to receive an inlay strip of a high thermal conductivity material (e.g., silver or copper). The strip of stainless steel substrate with inlay strip of high thermal conductivity material is next roll bonded to achieve a metallurgical bond between the inlay strip of high thermal conductivity material and the stainless steel substrate, typically with an overall thickness reduction of at least 50%. Next, the length of the roll bonded composite stainless steel strip incorporating an inlay of high thermal conductivity material is cut in half and the two composite strips are positioned together such that the outer edges are aligned and the inlays of high thermal conductivity material on both strips are facing each other. These two composite strips then are roll bonded together such that the inlay of high thermal conductivity is located within outer layers of the stainless steel substrate. This alternative approach eliminates the need for welding a three-layer laminate strip comprising stainless steel and a high thermal conductivity material to strips of stainless steel.

The printing and firing of the electrically insulative dielectric layer is followed by the thick-film printing and firing of an electrically resistive heating element on the surface of the electrically insulative dielectric layer within the heated portion of the blade. The thick-film printable heating element material has a temperature coefficient of electrical resistance of at least 1000 and preferably more than 3000 parts-per-million/degree C. over the range from 20 C to 600 C and a sheet resistance at 20 C of about 30 to 200 milliohms/square. Two or more electrically conductive leads are thick-film printed and fired on the electrically insulative dielectric layer within the region of the support member of the blade and extend into the region of the heated portion of the blade and overlap at the termini of the electrically resistive heating element to provide electrical communication between the leads and the heating element. The thick-film printable electrically conductive lead material has a sheet resistance of less than about 5 milliohms/square. An electrically insulative dielectric overcoat layer is thick-film printed and fired over the entire electrically resistive heater element as well as all but the most proximal portions of the electrically conductive leads. A short length of the electrically conductive leads at the proximal end of the support member portion of the blade are not covered with the electrically insulative dielectric overcoat layer to permit engagement of the proximal end of the electrically conductive leads with electrical contacts within the distal end of the handpiece.

The thick-film pastes selected for the printing of the electrically insulative dielectric layer, electrically resistive heating element, electrically conductive leads and electrically insulative dielectric overcoat layer have a firing temperature in the range from about 600 C to 900 C to enable operation of the heating element of thermal cutting surgical instrument at a temperature of at least 400 C, preferably at least 500 C. The thickness of the thick-film printed and fired electrically insulative dielectric layer (e.g., less than about 0.001 inch) is [a] thin enough to minimize the temperature gradient across the electrically insulative dielectric layer during the application of electrical power to the heating element and [b] thick enough to prevent electrical breakdown of the dielectric layer during the application of the maximum voltage differential to the heating element.

The heat capacity of the heated portion of the blade is advantageously minimized to reduce the time required to raise the temperature of the heated portion of the blade from room temperature to the preselected blade operating temperature required for the thermal cutting of tissue (e.g., about 500 C). The heat capacity of the heated portion of the blade is minimized by reducing the thickness and width of the heated portion of the blade to levels consistent with maintaining the ability of the structure of the heated portion of the blade to withstand contact pressure with tissue during the application of tamponade in combination with the heated portion of the blade to seal transected blood vessels. However, the minimum width of the heated portion of the blade must also be sufficiently wide to provide a sufficient surface area at the heating element/dielectric layer interface to maintain the maximum heat flux between the heating element and the first substrate within an acceptable level, for example not greater than about 250 watts/sq. cm. Preferably the heat capacity of the heated portion of blade is less than about 0.025 calories/C.

In a preferred embodiment of the present invention, a direct current (DC) voltage is applied to the terminals of one or more heating element segments located in the heated portion of the blade. Resistance-feedback control circuitry is incorporated within handpiece to maintain the heating element in the heated portion of the blade within a narrow band of temperature that only varies about 5 C above or below the preselected thermal cutting and blood vessel sealing temperature (e.g., 500 C).

In addition to incorporating all heating element temperature control circuitry within the handpiece, the handpiece also includes a pressure sensitive switch that energizes the heating element and maintains the heating element at the preselected thermal cutting and blood vessel sealing temperature as long as the pressure sensitive switch is depressed. Also, the handpiece incorporates display lights to indicate operating states of heated portion of blade. A first display light corresponds to a first operating state indicating that the blade ready to be heated. A second display light corresponds to a second state indicating that the blade is at the temperature required for thermal cutting of tissue and/or sealing of blood vessels. A third display light corresponds to a third state corresponding to a failed heating element requiring the operator to replace the currently used thermal cutting blade with a new sterile blade by removing the defective blade from the handpiece and inserting a new blade in its place.

In addition to display lights to indicate the functional state of the thermal cutting surgical instrument, the handpiece also may incorporate a sound generating element that provides an audible cue to the operator that the heating element is at the preselected temperature to effect thermal cutting and coagulation of tissue. The handpiece of the preferred embodiment incorporates a flexible, two-lead cable that extends from the handpiece to a simple, low-cost DC power supply of the type commonly used with laptop computers and other portable electronic devices. The DC power supply is removably connectable to any electrical outlet (e.g., 115 volt, 60 cycle line power) available in any operating room or surgery setting and provides a constant DC voltage to the resistance-feedback control circuitry, switch function and display lights incorporated within the handpiece. The remote DC power supply may include a single on/off power switch.

The present disclosure includes methods of manufacturing an electrically heated thermal cutting surgical blade, comprising the sequence of steps of:

a. providing a first substrate in the form of a laminate strip of first thickness having a core of a high thermal conductivity material having lateral faces surrounded by a pair of outer layers of metal having a high modulus of elasticity, having a coefficient of expansion that is similar to the electrically insulative dielectric layer and suitable for mechanical and/or chemical bonding to an electrically insulative dielectric layer;

b. providing a second substrate strip of second thickness of a low thermal conductivity material where first thickness and second thickness are preferably substantially the same and having a coefficient of expansion that is similar to the electrically insulative dielectric layer and suitable for mechanical and/or chemical bonding to an electrically insulative dielectric layer;

c. metallurgically joining, as by welding, the laminate strip of first substrate to the strip of second substrate along a longitudinal joint to form a composite strip incorporating both first and second substrates;

d. providing the composite strip with a smooth surface at the longitudinal joint;

e. perforating the composite strip to define at least one blade blank having a first region extracted or cut from the first substrate that functions as the heated portion of the blade and a second region extracted or cut from the second substrate that functions as the support member portion of the blade;

f. depositing a thin layer of an electrically insulative dielectric material on one side of the blade blank in both the first region and second region, the electrically insulative dielectric material having a thermal expansion coefficient in the range of the thermal expansion coefficient of the outer layers of the first region and the material of the second region;

g. depositing a thin layer of an electrically resistive material in a first pattern on the layer of electrically insulative dielectric material in the first region of the blade blank that functions as the heating element;

h. depositing a thin layer of an electrically conductive material in a second pattern on the layer of the electrically insulative dielectric material in the second region of the blade blank that functions as the electrical leads, the second pattern overlapping the first pattern of electrically resistive material dielectric so that the terminals of the heating element comprising electrically resistive material and distal terminals of electrical leads comprising electrically conductive material are in electrical communication;

i. depositing a thin electrically insulative dielectric overcoat layer over the first and second patterns of electrically resistive and electrically conductive materials except for a portion of the second pattern that is left exposed to accommodate completing an electrical contact between the electrically conductive leads and the electrical terminals of the handle and j. optionally depositing a thin coating of biocompatible material over the entire surface of the first and second region of the blade up to but distal to the portions of the electrically conductive leads not covered by the electrically insulative dielectric overcoat layer, the coating of biocompatible material not required in the event all materials of construction of the tissue contacting portions of the blade are biocompatible.

An advantage of the present invention is an improved surgical blade for the thermal cutting of tissue without the need for a surgically sharp cutting edge, and methods of making such blades. Another advantage is a durable blade having improved thermal delivery capabilities over a broad range of conditions encountered in the thermal cutting of tissue. A yet another advantage is a thermally regulated heated blade having a cutting region that is maintained at a nearly uniform temperature over the full range of surgical cutting conditions. A further advantage is a thermal cutting blade that permits sustained operation without adherence of tissue or coagulum during surgical use and without the need for a non-stick coating. A yet further advantage is an electrically heated blade that reduces conduction of heat from the heated portion of the surgical blade to the blade supporting handpiece. Another advantage is an electrically heated surgical blade having thick-film printed electrical leads characterized by a low electrical resistance to reduce Joulean heating within a blade support member by resistive losses in the electrical leads. A further advantage is a surgical instrument for the thermal cutting of tissue whose heated portion of the blade has a heat capacity that is sufficiently low to enable heat up of the blade from room temperature to a thermal cutting temperature within about one second. Another advantage is the elimination the of a costly control system external to the handpiece. A further advantage is a method of manufacturing a surgical blade to maximize temperature uniformity of the heated portion of the blade and minimize thermal conduction from the heating element and tissue cutting regions of the blade to the handpiece supporting the blade. These and other advantages will be apparent to the skilled artisan based on the present disclosure.

BRIEF DESCRIPTION OF THE DRAWINGS

For a fuller understanding of the nature and advantages of the present method and process, reference should be had to the following detailed description taken in connection with the accompanying drawings, in which:

FIG. 2 is a side view of a thermal cutting blade illustrating the distal heated portion of the blade and the proximal support member portion of the blade constructed in accordance with the present disclosure;

FIG. 2A is a detailed view of the region of the overlap between an electrically conductive lead and a heating element terminal;

FIG. 2B is a cross-sectional view of the support member portion of the blade illustrating the second substrate, electrically insulative dielectric layer, electrically conductive lead, electrically insulative dielectric overcoat layer and biocompatible coating layer (if required);

FIG. 3 is a cross-sectional view taken along line 3-3 of FIG. 2;

FIG. 3A is an enlarged view of an area in FIG. 3;

FIG. 4 is a cross-sectional view taken along line 4-4 of FIG. 2;

FIG. 4A is an enlarged view of a cross-sectional view taken in a region between adjacent electrically conductive leads illustrating second substrate on which electrically insulative dielectric layer, electrically conductive lead, electrically insulative overcoat layer and biocompatible coating layer (if required) are sequentially disposed in in FIG. 4;

FIG. 5 is a cross-sectional view taken along line 5-5 of FIG. 2;

FIG. 5A is an enlarged view of a cross-sectional view taken in a region between adjacent electrically conductive lead and sense lead illustrating second substrate on which electrically insulative dielectric layer, electrically conductive power lead, electrically conductive sense lead, electrically insulative overcoat layer and biocompatible coating layer (if required) are sequentially disposed in FIG. 5;

FIG. 6 is a cross-sectional view taken along line 6-6 of FIG. 2;

FIG. 6A is an enlarged view of a cross-sectional view taken in a region between adjacent electrically conductive leads illustrating second substrate on which electrically insulative dielectric layer, electrically conductive power lead, electrically conductive sense lead, electrically insulative overcoat layer and biocompatible coating layer (if required) are sequentially disposed in FIG. 6;

FIG. 7A-7C is a cross sectional view taken at sequential stages of grinding, inlay of thermally conductive strip, roll bonding subassembly and final roll bonding of subassemblies to produce strip of stainless steel substrate incorporating inlay of high thermal conductivity material;

FIGS. 9A-9D combine as labeled thereon to provide a flow chart describing the manufacture of the thermal cutting surgical blades as seen at FIGS. 2-7.

The drawings will be described in greater detail in the following detailed description.

DETAILED DESCRIPTION

Figure 1:
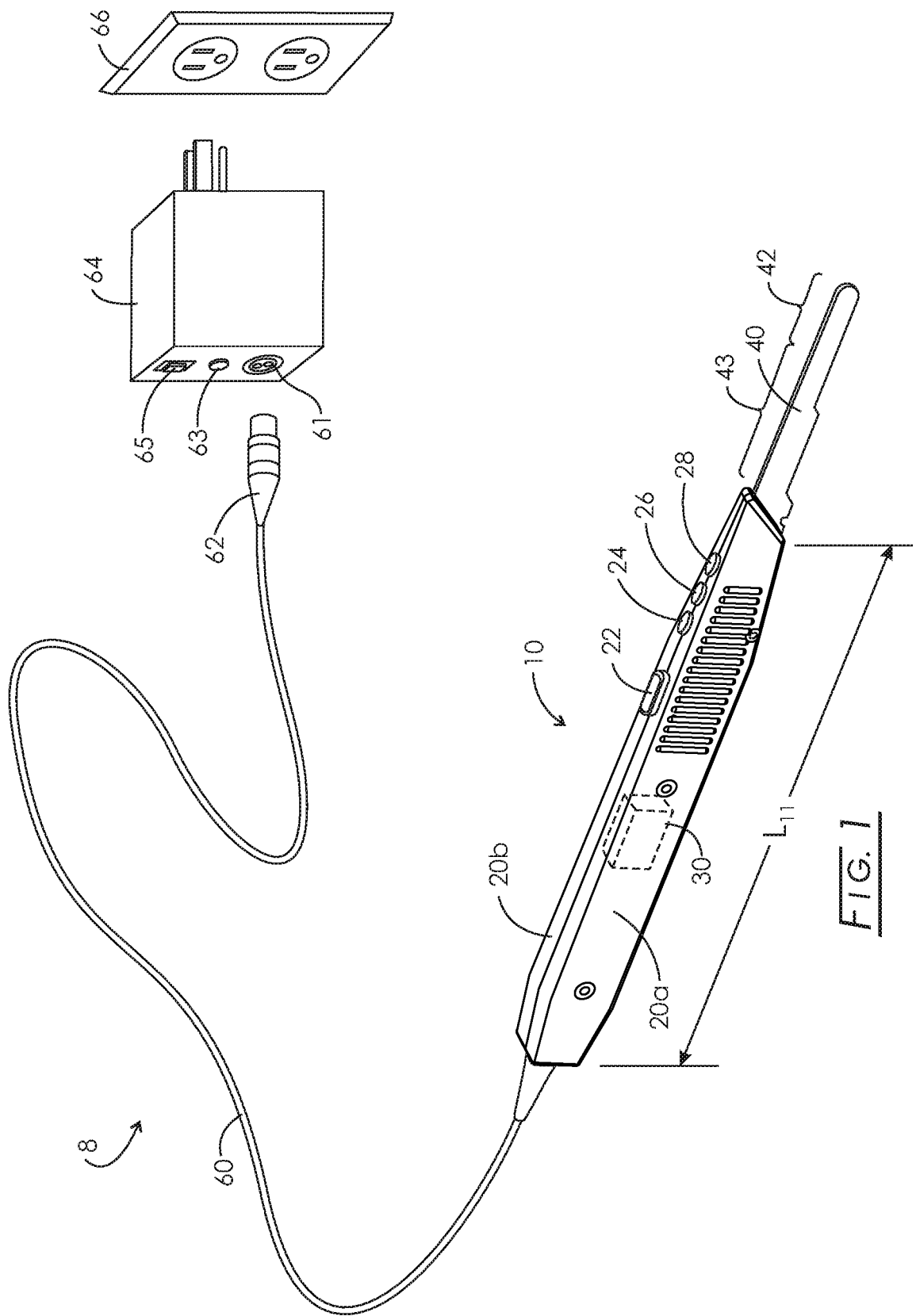
FIG. 1 is a perspective view of a thermal cutting surgical instrument comprising a thermal cutting blade, handpiece, cable and DC power supply.

Referring to FIG. 1, thermal cutting surgical instrument 8 is shown comprising a blade 40 constructed in accordance with the present disclosure is described. Surgical blade 40 is shown inserted into a handpiece 10 for supporting blade 40, and is removably attachable to receptacle 61 located on substantially constant voltage, direct current (DC) power supply 64 via a low-cost, two-wire cable 60 and plug 62. The substantially constant voltage, direct current (DC) power supply 64 seen in FIG. 1 is similar to the type used for laptop computers and other similar electronic devices requiring a source of substantially constant DC voltage and may include an on/off switch 65 and power supply light 63 that illuminates (e.g., red LED) when power supply is turned on. The power source may be, for example, one such as the medical-grade AC-DC power supply, Model ETMA24025OUD manufactured by CUI, Inc. (Tualatin, Oreg.) that delivers a maximum DC current of 2.5 amps at a substantially constant DC voltage of 24 volts when removably attached to electrical wall outlet 66 (e.g., 115 volt, 15 amp, 60 Hz standard line power outlet). This example medical grade power supply manufactured by TUI, Inc. costs about $40 and replaces controller/power supplies required for prior art electrosurgery and other radiofrequency powered surgical instruments that cost about $3,000 to $5,000 to manufacture and that generally are sold to hospitals and surgery centers for $20,000 or more.

Still referring to FIG. 1, handpiece 10 includes pressure-sensitive switch 22 that applies electrical power to heating element (not shown) located in heated portion 42 of blade 40 and maintains the temperature of the heating element (not shown) at the preselected thermal cutting temperature (e.g., 500 C+/−5 C) as long as the pressure-sensitive switch 22 is depressed.

Still referring to FIG. 1, handpiece 10 also includes visual cues to indicate the state of operation of the thermal cutting surgical instrument 8. By way of example, handpiece 10 may incorporate small display lights in the form of light emitting diodes (LEDs) to indicate the operating states of the heated portion of blade. For example, a first display light 24 (e.g., green LED) on handpiece 40 corresponds to a first operating state indicating that blade 40 is properly connected to handpiece 40 and power supply 64 and is ready to be heated. A second display light 26 (e.g., yellow LED) on handpiece 10 corresponds to a second state indicating that the heating element located in heated portion 42 of blade 40 is energized and that the heated portion 42 of blade 40 is at the temperature required for thermal cutting of tissue and/or sealing of blood vessels. A third display light 28 (e.g., red LED) on handpiece 10 corresponds to a third state indicating that the heating element located in heated portion 42 of blade 40 has failed and requires that the operator replace the defective blade 40 with a new blade 40.

A defective or failed blade 40 is detected by electrical resistance measuring circuitry incorporated in control circuit 30 within handpiece 10 as represented in FIG. 1. The electrical resistance measuring circuitry within control circuit 30 continuously monitors the electrical resistance of the heating element at all times after blade 40 is inserted into handpiece 10, plug 62 at proximal end of cable 60 is removably attached to power supply 64 at receptacle 61 and power supply 64 is turned on at on/off switch 65. If the electrical resistance of the heating element during any time during use is outside a preselected resistance range (e.g., 5 to 30 ohms), then the third display light 28 will be illuminated indicating that the heating element located in heated portion 42 of blade 40 is defective and needs to be replaced.

In addition to display lights to indicate the functional state of thermal cutting surgical instrument 8, handpiece 10 also may incorporate a sound generating element (not shown) that provides an audible cue to the operator that the heating element disposed on the heated portion 42 of blade 40 is at the preselected temperature to effect thermal cutting and coagulation of tissue.

Referring now to FIG. 2, a top view of blade 40 is shown having a heated portion 42 and support member portion 43. The heated portion 42 of blade 40 comprises a first substrate 67 comprising a core 72 and claddings 70a and 70b onto which an electrically insulative dielectric layer 46 is disposed (and also extends into support member portion 43 of blade 40) followed by the deposition of an electrically resistive heating element 48 and covered by an electrically insulative dielectric overcoat 74 (not shown) and optional thin outer layer of biocompatible coating 82 (not shown). The biocompatible coatings may include materials such as, for example, titanium nitride, titanium aluminum nitride, chromium nitride, zirconium nitride, gold, silver and, if maximum operating temperature is below 500 C, Parylene HT®. In this regard, Parylene HT® coatings are available from Specialty Coating Systems, Inc., Indianapolis, Ind. Thin film gold coatings are available, by way of example, from LGA Thin Films, Inc., Santa Clara, Calif. Nitride-based biocompatible coatings are available from Dayton Coating Technologies, Dayton, Ohio.

Still referring to FIG. 2, top view of blade 40 also reveals support member portion 43 of blade 40. The support member portion 43 of blade 40 comprises second substrate material 80 onto which electrically insulative dielectric layer 46 is disposed followed by the deposition of electrically conductive power leads 52a-52b and electrically conductive sense leads 54a-54b and covered over most of their lengths except for a short length, L9, by an electrically insulative dielectric overcoat 74 (not shown) and optional thin outer layer of biocompatible coating 82 (not shown).

Referring now to FIG. 2A, a top view of an overlap region 50a is seen in greater detail where electrically conductive power lead 52a overlaps terminal 47a of electrically resistive heating element 48 to provide electrical communication between the electrically conductive power lead 52a and heating element 48 and covered by an electrically insulative dielectric overcoat 74 (not shown) and optional thin outer layer of biocompatible coating 82 (not shown).

Referring now to FIG. 2B, a cross-sectional view of the proximal end of support member portion 43 of blade 40 is seen whereon an electrically insulative dielectric layer 46 is disposed followed by the deposition of electrically conductive power lead 52a. As seen in FIG. 2B, electrically insulative dielectric overcoat 74 ends prior to the proximal end of electrically conductive power lead 52a so that a short length, L9, of electrically conductive power lead 52a at the proximal end of the support member portion 43 of the blade 40 is not covered with the electrically insulative dielectric overcoat 74 to permit engagement of the proximal end of the electrically conductive power lead 52a with a corresponding sliding electrical contact within the distal end of the handpiece 10 (not shown). Also, as seen in FIG. 2B, the outer layer of optional biocompatible coating 82 (if needed) ends distal to the proximal end of electrically insulative dielectric overcoat 74 since a preferred biocompatible coating 82 may be electrically conductive and would otherwise result in an unwanted electrically conductive pathway among electrically conductive power leads 52a-52b and electrically conductive sense leads 54a-54b. The arrangement of the electrically insulative dielectric overcoat 74 and the outer layer of optional biocompatible coating 82 seen in FIG. 2B for electrically conductive power lead 52a also applies the proximal ends of electrically conductive power lead 52b and electrically conductive sense leads 54a-54b.

Referring now to FIG. 3, a cross-sectional view 3-3 of FIG. 2 is seen representing the heated portion 42 of blade 40. As seen in FIG. 3, first substrate 67 is in the form of a laminate that comprises a core 72 of high thermal conductivity material on which a first cladding 70a is disposed on its top face to form first surface 69 of first substrate 67 and on which a second cladding 70b is disposed on its bottom face to form second surface 73 of first substrate 67. Preferably, the thermal conductivity of metal selected for core 72 is greater than 2 watt/cm-C, more preferably greater than 3 watt/cm-C. The first and second claddings 70a, 70b are selected from among metals having a high modulus of elasticity, having a coefficient of expansion that is similar to the electrically insulative dielectric layer 46 and that are suitable for attaining good adhesion to electrically insulative dielectric layer 46. As seen in FIG. 3, electrically resistive heating element legs 48a-48d of electrically resistive heating element 48 are disposed on electrically insulative dielectric layer 46 in a spaced apart arrangement as also seen in FIG. 2. The electrically resistive heating element legs 48a-48d of electrically resistive heating element 48 are covered by an electrically insulative dielectric overcoat 74 (not shown) that is covered, in turn, by outer layer of biocompatible coating 82, if required (not shown).

By way of example and referring to FIGS. 2 and 3, an unsharpened, blunt edge of blade 40 may have facets 71a, 71b that extend along length L10 of heated portion 42 of blade 40. The facets 71a, 71b form an unsharpened edge shape that minimizes the applied force required for the thermal cutting of tissue while improving the transfer of heat and associated degree of coagulation achieved at the point at which blood vessels within the tissue are being severed.

Referring now to the exploded view provided in FIG. 3A, the cross-section 3-3 shown in FIG. 3 is seen in greater detail. As seen in FIG. 3A, electrically insulative dielectric layer 46 is disposed on cladding 70a that forms first surface 69 of first substrate 67. Electrically resistive heating element leg 48a is disposed on electrically insulative dielectric layer 46 and the electrically insulative dielectric layer 46 and electrically resistive heating element leg 48a are both covered by electrically insulative dielectric overcoat 74 that is covered, in turn, by outer layer of biocompatible coating 82, if required.

Referring now to FIG. 4, a cross-sectional view 4-4 of FIG. 2 is seen representing the support member portion 43 of blade 40. As seen in FIG. 4, second substrate is selected from among metals having a low thermal conductivity, high modulus of elasticity, having a coefficient of expansion that is similar to the electrically insulative dielectric layer 46 and that are suitable for attaining good adhesion to electrically insulative dielectric layer 46. Preferably, the thermal conductivity of metal selected for second substrate 80 is less than 0.6 watt/cm-C, more preferably less than 0.3 watt/cm-C.

As seen in FIG. 4, electrically conductive power leads 52a, 52b are disposed on electrically insulative dielectric layer 46 in a spaced apart arrangement as also seen in FIG. 2. The electrically conductive power leads 52a, 52b are covered by an electrically insulative dielectric overcoat 74 (not shown) that is optionally covered, in turn, by outer layer of biocompatible coating 82 (not shown).

Referring now to the enlarged view provided in FIG. 4A, the cross-section 4-4 shown in FIG. 4 is seen in greater detail. As seen in FIG. 4A, electrically insulative dielectric layer 46 is disposed on second substrate 80. Electrically conductive power lead 52a is covered by an electrically insulative dielectric overcoat 74 that is optionally covered, in turn, by an outer layer of biocompatible coating 82.

Referring now to FIG. 5, a cross-sectional view 5-5 of FIG. 2 is seen representing the support member portion 43 of blade 40. As seen in FIG. 5, electrically conductive power leads 52a, 52b and electrically conductive sense lead 54a are disposed on electrically insulative dielectric layer 46 in a spaced apart arrangement as also seen in FIG. 2. The electrically conductive power leads 52a, 52b and electrically conductive sense lead 54a are covered by an electrically insulative dielectric overcoat 74 (not shown) that is optionally covered, in turn, by outer layer of biocompatible coating 82 (not shown).

Referring now to the partial view provided in FIG. 5A, the cross-section 5-5 shown in FIG. 5 is seen in greater detail. As seen in FIG. 5A, electrically insulative dielectric layer 46 is disposed on second substrate 80. Electrically conductive power lead 52a, electrically conductive sense lead 54a and intervening surface of electrically insulative dielectric layer 46 are covered by an electrically insulative dielectric overcoat 74 that is optionally covered, in turn, by an outer layer of biocompatible coating 82.

Referring now to FIG. 6, a cross-sectional view 6-6 of FIG. 2 is seen representing the support member portion 43 of blade 40. As seen in FIG. 6, electrically conductive power leads 52a, 52b and electrically conductive sense leads 54a, 54b are disposed on electrically insulative dielectric layer 46 in a spaced apart arrangement as also seen in FIG. 2. The electrically conductive power leads 52a, 52b and electrically conductive sense leads 54a, 54b are covered by an electrically insulative dielectric overcoat 74 (not shown) that is covered, in turn, by outer layer of optional biocompatible coating 82 (not shown).

Referring now to the partial view provided in FIG. 6A, the cross-section 6-6 shown in FIG. 6 is seen in an enlarged view. As seen in FIG. 6A, electrically insulative dielectric layer 46 is disposed on second substrate 80. Electrically conductive power lead 52a, electrically conductive sense lead 54a and intervening surface of electrically insulative dielectric layer 46 are covered by an electrically insulative dielectric overcoat 74 that is optionally covered, in turn, by an outer layer of biocompatible coating 82.

Figure 7:
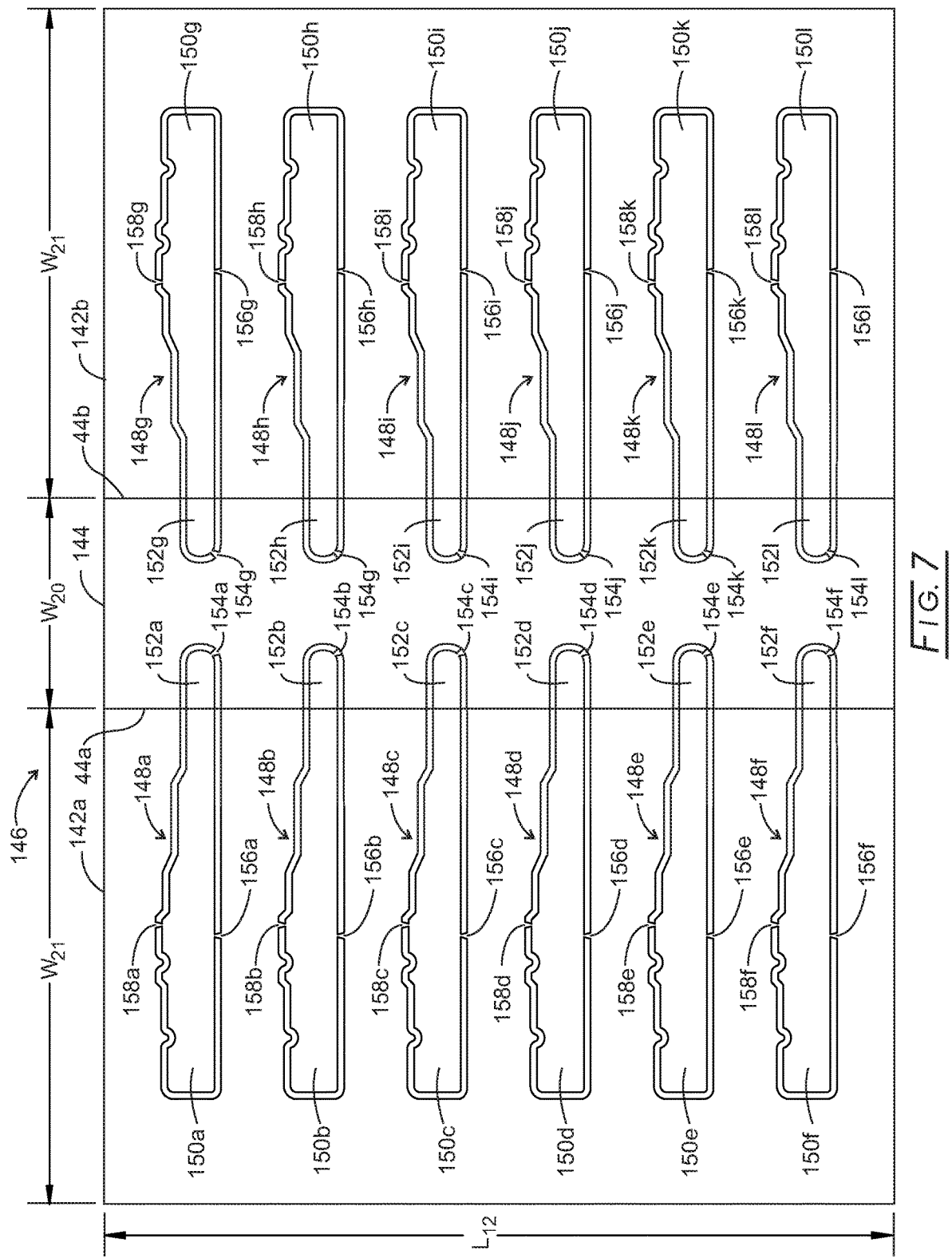
FIG. 7 is a top view of a composite strip incorporating laminate strip of first substrate joined along either edge to a strip of second substrate manufactured in accordance with the methods of the present disclosure and illustrating partially perforated blade blanks.

By way of example and referring to FIG. 7, blade blanks 148a-148l may be obtained by perforating composite three-component sheet 146. The composite three-component sheet 146 comprises a three-layer laminated metal strip 144 having width, W20, length, L12, and thickness, t1, that is welded along both longitudinal edges to single-layer metal strips 142a, 142b having widths, W21, lengths, L12, and thicknesses, t1. For example, the composite three-component sheet 146 may have width, W20, of 1.00 inch and length, L12, of 6.00 inch with a total thickness, t1, of 0.020 inch. The three-layer laminated strip 144 may be formed by roll bonding stainless steel Type 430 strip on both lateral surfaces of a high thermal conductivity silver core strip to produce a three-layer laminate metal strip 144 having a 0.003-inch thick cladding of stainless steel Type 430 on either face of a 0.014-inch thick high thermal conductivity silver core, as seen in cross-sectional view in FIG. 3. Alternatively, copper may be used in place of silver for core 72. The single-layer strips 142a, 142b may be stainless steel Type 430 and may have widths, W21, of 2.50 inch and lengths, L12, of 6.00 inch with a total thickness, t1, of 0.020 inch.

Still referring to FIG. 7, perforation of composite three-component sheet 146 may be performed, by way of example, using commonly available processes such as electro-discharge machining, die punching or photochemical machining. For example, if photochemical machining is used, small attachment points or ligaments 154a-154l, 156a-156l and 158a-158l enable the blade blanks 148a-148l to be supported within the perforated sheet until they are mechanically separated, for example, by deflecting blade blanks 148a-148l from the plane of composite three-component sheet 146. As seen in FIG. 7, each defined blade blank 148a-148l comprises a proximal portion 150a-150l and distal portion 152a-152l joined together along weld lines 44a, 44b. The distal portion 152 of blade blank 148 represents first substrate 67 of blade 40. The proximal portion 150 of blade blank 148 represents second substrate 80 of blade 40.

Figure 7D:
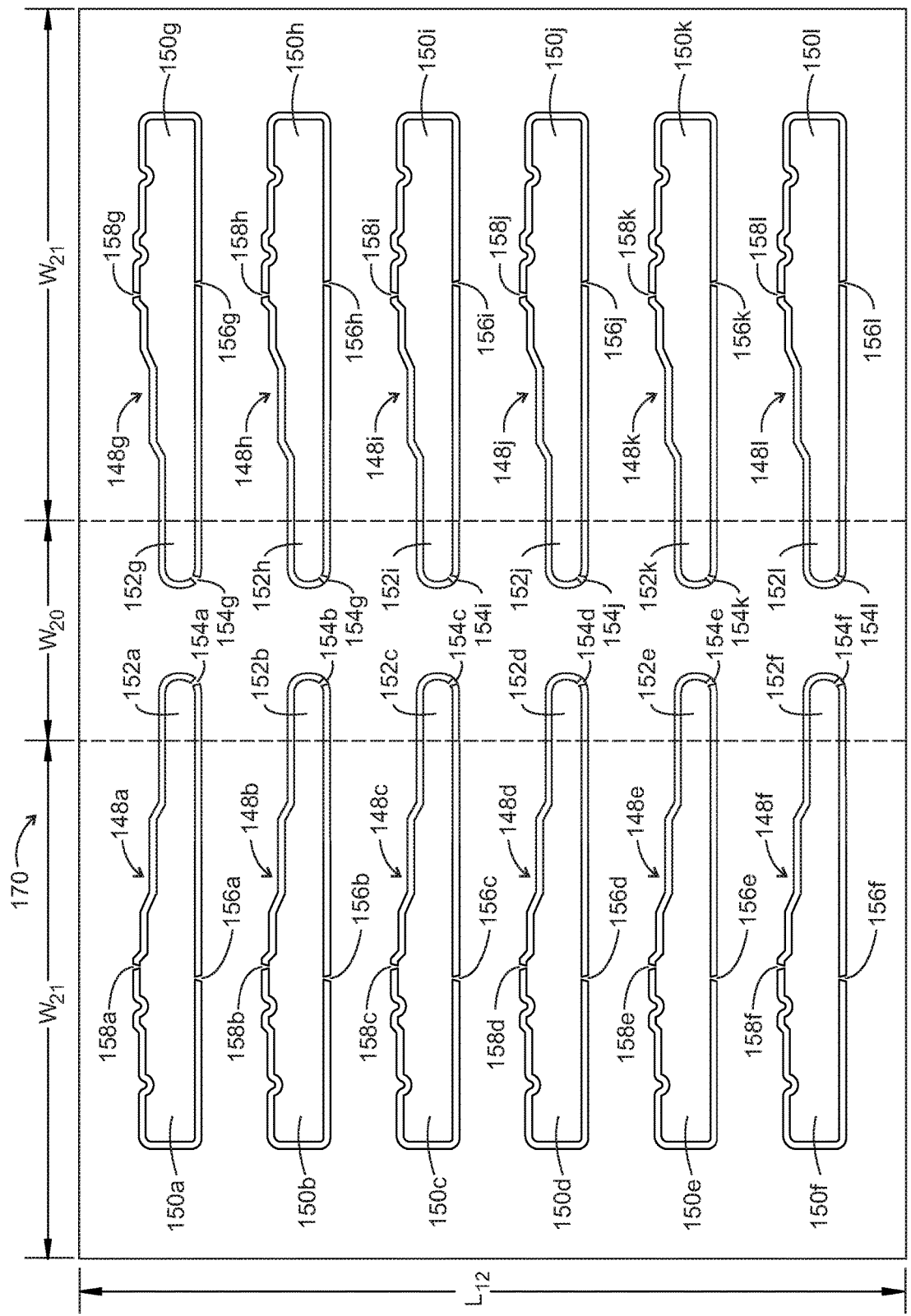
FIG. 7D is a top view of a composite strip of stainless steel substrate incorporating inlay of high thermal conductivity material manufactured by roll bonding in accordance with the methods of the present disclosure and illustrating partially perforated blade blanks.

Alternatively, a weld-free composite two-component sheet 170 seen in FIG. 7D can be manufactured by an accumulative roll bonding process as seen in FIGS. 7A-7C. In regard to roll bonding stainless steel strips together, refer to Ruppert, M., et al., Ultrafine-Grained Austenitic Stainless Steels X4CrNi18-12 and X8CrMnNi19-6-3 Produced by Accumulative Roll Bonding. Metals 2015; 5:730-742. Unlike composite three-component sheet 146 seen in FIG. 7, the manufacturing process for the weld-free composite two-component sheet 170 seen in FIG. 7D does not require welding (e.g., electron beam welding or laser welding) stainless steel strips along either edge to a three-layer laminate metal strip 144 as seen along weld lines 44a and 44b of FIG. 7.

Referring to FIG. 7A, a slot having width W20 and depth t9 is formed in stainless steel strip 160a of thickness t8 and width W21+W20+W21. By way of example, the slot may be formed in stainless steel strip 160a having width W20 and thickness t9 by abrasive grinding or skiving. Next, a metal inlay strip 166a of thermally conductive material (e.g., silver or copper) having a width slightly less than slot width W20 (e.g., a width of W20—0.020 inch) and thickness t9 is placed within the slot in stainless steel strip 160a. The stainless steel strip 160a and metal inlay strip 166a are roll bonded to produce composite strip with inlay 166a having width W20 as seen at 161a in FIG. 7A. The first step of the roll bonding process produces a composite strip with inlay 161a, the composite strip having an overall width W21+W20+W21 and length L14 ranging from several feet to 100 feet or more. The above process is repeated to produce an identical composite strip with inlay 166b having width W20 as seen at 161b in FIG. 7B. The second step of the roll bonding process produces a composite strip having an overall width W21+W20+W21 and length L14 as seen in FIG. 7B. Alternatively, a single composite strip with inlay 161a may be cut in half to obtain identical composite strip with inlay 161b as seen in FIG. 7B.

The two roll bonded composite strips with inlays 161a and 161b are next positioned such that metal strip inlays 166a and 166b facing each other so that the edges of stainless steel strips 160a and 160b and metal strip inlays 166a and 166b are aligned as seen in FIG. 7C. These two composite strips with inlays 161a and 161b are next roll bonded together to form the weld-free two-component strip incorporating composite metal inlay strip 168 with a roll bonded metallurgical bond line 162 as seen in FIG. 7C. This roll bonding manufacturing process eliminates the need for edge welding stainless steel strips to the three-layer laminate as seen in FIG. 7 thereby assuring a smooth surface on the extracted blade blank 148 preferred for subsequent thick-film printing of electrically insulative dielectric layer 46.

Referring to FIG. 7D, the roll bonded weld-free two-component strip as seen in FIG. 7C may, by way of example, be cut into lengths L12 to form weld-free two-component sheet 170. By way of example and referring to FIG. 7D, blade blanks 148a-148l may be obtained by perforating weld-free two-component sheet 170 using a process such as electro-discharge machining. The weld-free two-component sheet 170 seen in FIG. 7C comprises a composite of roll bonded stainless steel strips 160a and 160b incorporating metal inlay strips 166a and 166b of high thermal conductivity material (e.g., silver or copper) to form composite metal inlay strip 168. As seen in FIGS. 7C and 7D, composite metal inlay strip 168 has width W20, length L12 and thickness t3. The composites of roll bonded stainless steel strips 160a and 160b extending on either side of the composite metal inlay strip 168 have widths W21, length L12 and thickness t1. For example, the weld-free two-component sheet 170 may have width W20 of 1.00 inch, width W21 of 2.0 inches and length L12 of 6.00 inches with a total thickness t1 of 0.025 inch.

Yet another method to produce blade blanks 148 incorporating a high thermal conductivity material (e.g., silver or copper) in the heated portion 42 of blade 40 with first and second claddings 70a and 70b of stainless steel (e.g., stainless steel 430) involves a three step roll bonding process as described below. In the first step, a strip of steel (e.g., low-carbon 1020 steel, 0.060 inch thick×3.00 inch wide×50 feet long) is placed on top of and registered with a strip of stainless steel (e.g., stainless steel 430, 0.020 inch thick× 3.00 inch wide×50 feet long) and roll bonded together between two rolls to obtain a 50% reduction in the laminate thickness. Following this first roll bonding process in this first step, the thickness of the steel layer is reduced to 0.030 inch and the thickness of the stainless steel layer is reduced to 0.010 inch and the overall length of the roll bonded steel/stainless steel laminate is increased to about 100 feet as a result of the 50% thickness reduction. In the second step of this process, by way of example, a 0.030-inch deep×0.50 inch wide slot is formed along the full length of the steel layer at a distance of 0.50 inch from one edge of the roll bonded strip. In the third step, a strip of high thermal conductivity material (e.g., silver or copper) having a thickness, by way of example, of 0.030 inch and width 0.480" is inlayed into the slot formed in the second step followed by placing a strip of stainless steel (e.g., stainless steel 430, 0.010 inch thick×3.00 inch wide×nominally 100 feet long) and registering the stainless steel strip against the surface of steel and the surface of the inlay of a high thermal conductivity material (e.g., silver or copper) and roll bonded together between two rolls to obtain a 50% reduction in the three-component laminate thickness. Following roll bonding in this third step, the thicknesses of the steel layer and high thermal conductivity material are reduced to 0.015 inch wherein in both the steel and the high thermal conductivity material are disposed between first and second claddings 70a and 70b of stainless steel. Following this second roll bonding process, the thickness of the stainless steel layer is reduced to 0.005 inch and the overall length of the roll bonded steel/stainless steel laminate with an inlay of high thermal conductivity material is increased to about 200 feet as a result of the 50% thickness reduction. The finished roll bonded composite strip is similar to that shown in FIG. 7C except that an intermediate layer of steel is employed between the stainless steel layers to improve the strength of the bond between the first and second cladding layers 70a and 70b during a roll bonding process.

Once the individual blade blanks 148a-148l are separated from composite three-component sheet 146, they may be placed on a custom-designed setter (not shown) that precisely positions and holds each blade blank 148 in a preselected position within an array with the left side of each blade blank 148 facing up as illustrated in the side view of blade 40 seen in FIG. 2. The precise positioning of each blade blank 148 in a preselected position within an array enables the subsequent and sequential screen printing and firing of thick-film pastes selected for the electrically insulative dielectric layer 46, electrically resistive heating element 48, electrically conductive power leads 52a, 52b as well as sense leads 54a, 54b and, lastly, the electrically insulative dielectric overcoat 74. The screens used in the thick-film printing of the layers are fabricated so that they accurately register with the precise locations of each the blade blanks 148 within the array in the setter. The setter advantageously may be manufactured using a material that can withstand repeated exposure to the firing temperature for the aforementioned thick-film pastes. By way of example, the thick film setter may be a stainless steel 430 plate or silicon nitride plate containing multiple machined blade-shaped cavities and indexing pins to precisely position each blade blank 148 in a preselected position within the array in the setter that registers with the corresponding patterns on the screens used for screen printing. The machined stainless steel 430 plate may be optionally coated with 1 to 4 microns of Aluminum Titanium Nitride to minimize oxidation during multiple firing cycles in air at temperatures up to 850 C. In this regard, aluminum titanium nitride oxidation-resistant coatings are available from Advanced Coating Service located in Rochester, N.Y.

By way of example and returning now to FIGS. 1-6, the thick-film paste used in the thick-film printing of the electrically insulative dielectric layer 46 may be a commercially available screen-printable paste from ESL Electroscience (King of Prussia, Pa.) known as Product No. ESL 4931. This thick film paste is optimally fired at a peak temperature of 850 C in air and produces an electrically insulative dielectric layer thickness of about 0.0010 inch.

By way of example and still referring to FIGS. 1-6, the thick-film paste used in the thick-film printing of the electrically resistive heating element 48 may be a commercially available screen-printable paste from ESL Electroscience (King of Prussia, Pa.) known as Product No. ESL 29130. This thick-film paste has a electrical sheet resistance of 0.100 ohm/square and a temperature coefficient of resistance of 3,320 ppm/C. This thick-film paste is optimally fired at a peak temperature of 850 C in air and produces an electrically resistive layer thickness of about 0.0008 inch.

By way of example and still referring to FIGS. 1-6, the thick-film paste used in the thick-film printing of the electrically conductive power leads 52a, 52b and electrically conductive sense leads 54a, 54b may be a commercially available screen-printable paste from ESL Electroscience (King of Prussia, Pa.) known as Product No. ESL 9695-G. This thick-film paste has an electrical sheet resistance of 0.006 ohm/square. This thick-film paste is optimally fired at a peak temperature of 850 C in air and produces an electrically conductive layer thickness of about 0.0005 inch.

By way of example and still referring to FIGS. 1-6, the thick-film paste used in the thick-film printing of the electrically insulative dielectric overcoat 74 may be a commercially available screen-printable paste from ESL Electroscience (King of Prussia, Pa.) known as Product No. ESL 4931. This thick film paste is optimally fired at a peak temperature of 850 C in air and produces an electrically insulative dielectric layer thickness of about 0.0010 inch.

Still referring to FIGS. 1-6, an optional biocompatible coating 82 may be disposed over the thick-film printed and fired electrically insulative dielectric overcoat 74. A biocompatible coating 82 will be required along the exposed core 72 of heated portion 42 of blade 40 if copper or a copper alloy is used as the high thermal conductivity material for core 72 owing to the known cytotoxicity of copper relative to human cells. In addition, a biocompatible coating 82 will also be required if the material used for the first and second claddings 70a and 70b is a material that does not meet the biocompatibility requirements for materials that come into contact with tissue or blood during surgical procedures.

In a preferred embodiment, stainless steel type 430 may be advantageously selected for use as the first and second claddings 70a and 70b, a material known to meet biocompatibility requirements with respect to contact with tissue or blood based on its composition. As seen in FIG. 3, advantageously selecting silver as the high thermal conductivity material for core 72 of the heated portion 42 of blade 40 in combination with first and second claddings 70a and 70b of a known biocompatible material such as stainless steel type 430 eliminates the need for any biocompatible coating 82. As a consequence, the complexity and cost of manufacturing blade 40 of the thermal cutting surgical instrument 8 is reduced as well as the risk of failure of the biocompatible coating 82 during surgical use. Potential failure mechanisms for the biocompatible coating 82 may include cracking of the coating or loss of adhesion with associated separation of potions of the biocompatible coating 82 from the blade 40. The rapid temperature rise of the heated portion 42 of blade 40 from room temperature to temperatures of 500 C or higher will occur multiple times during surgical use and could increase the possibility that the integrity of the biocompatible coating 72 may be compromised. For this reason, the application of a biocompatible coating that can maintain its barrier integrity increases the cost and complexity of its proper selection and deposition on blade 40.

By way of example of a biocompatible coating, if required, a coating of titanium nitride or aluminum titanium nitride having a preferred thickness in the range from 1 to 5 microns may be applied over the full length of the thick-film printed blade and all surfaces of blade 40 up to but not closer than a set back distance, L13 of 0.10 to 0.20 inch from the proximal edge of the electrically insulative dielectric overcoat 74 as seen in FIG. 2B. This set back distance, L13 is required to avoid creating any unwanted electrical conduction paths between the electrically conductive power leads 52a, 52b and electrically conductive sense leads 54a, 54b.

Figure 8:
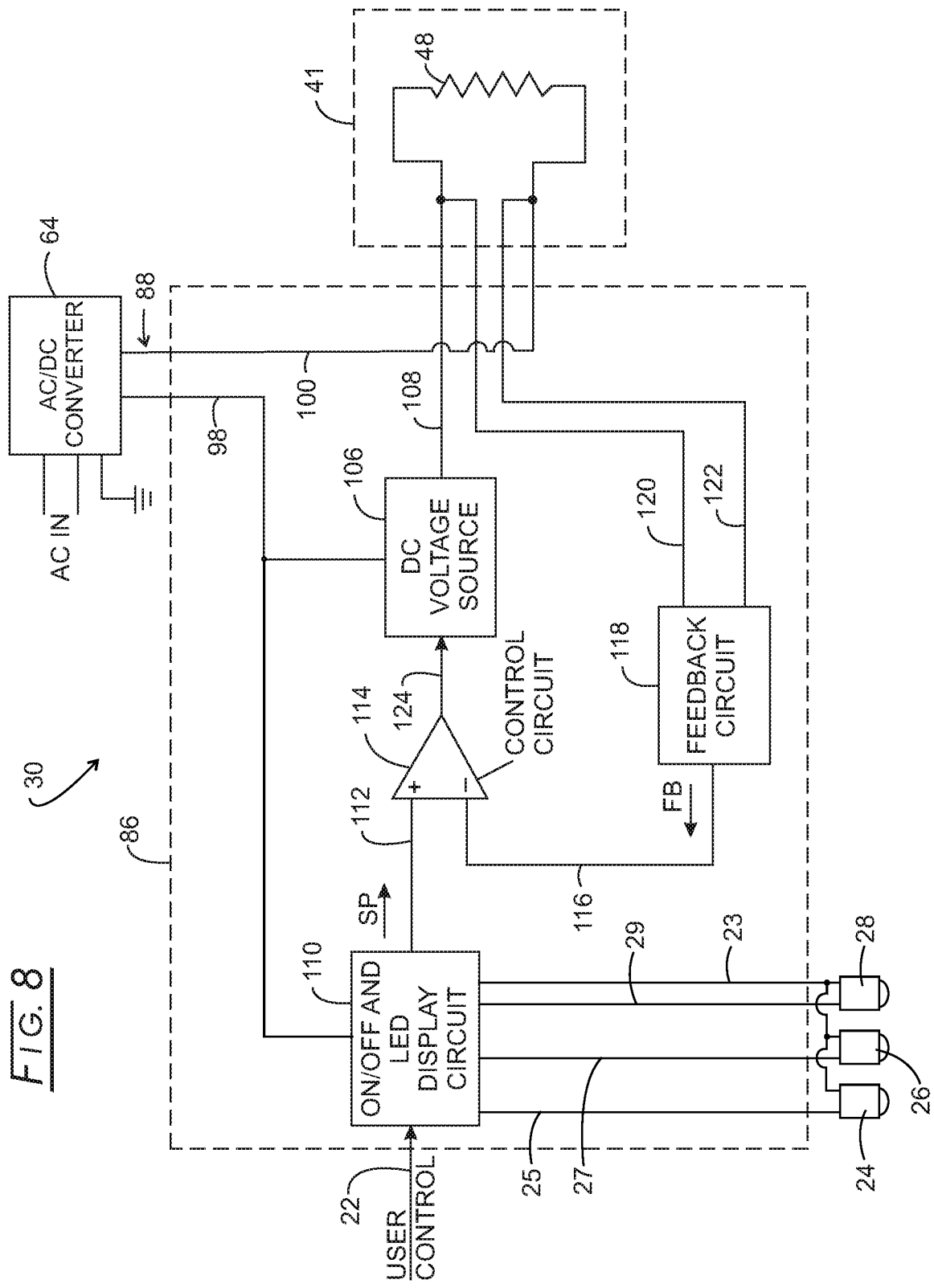
FIG. 8 is a schematic diagram is an example of a control circuit that may be employed within the handpiece of FIG. 1.

Referring now to FIG. 8, a simplified schematic representation of the control circuit 30 is set forth. As seen in FIG. 8, the first lead 88 and second lead 98 carrying electrical current from a constant direct current (DC) voltage source having a substantially constant voltage output within power supply 64 via cable 60 seen in FIG. 1. A thermal cutting blade 40 is represented at dashed boundary 41 with a symbolic electrically resistive heating element 48 drivably coupled from a variable DC voltage source 106 via line 108 and further being coupled with first lead 88. User control as evolved from the pressure-sensitive switch 22 is represented with the same numeration in conjunction with an arrow extending to on/off, pre-selected set point temperature and display functions control unit as represented at block 110. By way of example, control unit 110 may be a programmable gate array to provide a set point control signals as represented at line 112 to a comparing function represented symbolically at 114. The opposite input to comparison function 114 is from line 116 and a feedback circuit 118. Feedback circuit 118, in turn, as represented at lines 120 and 122 derives a voltage tap from lines 108 and 100 to develop a temperature feedback related signal at line 116. A resultant correction signal then is developed from comparing function 114 at line 124 to correspondingly adjust DC voltage source 106 and regulate the power delivered to the electrically resistive heating element 48 to maintain its temperature at a single preselected level (e.g., 500 C) by maintaining the electrical resistance of the electrically resistive heating element 48 at a pre-selected multiple of the room temperature resistance of the electrically resistive heating element 48.

By way of example of the resistance feedback control method of the present disclosure, assume that the room temperature resistance, R22, of the electrically resistive heating element 48 for a particular blade 40 is 5.00 ohms and the room temperature is assumed to be 22 C. The temperature coefficient of resistance (TCR) of the electrically resistive heating element 48 is known for a selected thick-film printed and fired paste composition (e.g., a TCR of 3,320 ppm/C for ESL Product No. 29130). Based on these values, the set-point resistance, Rsp at the preselected set-point temperature, Tsp of 500 C is a fixed multiple of the room temperature resistance, R22 based on the following equation:

$$Rsp = R22*(1+TCR*[Tsp-22 \ C]) \quad \text{(Equation 2)}$$

Rearranging Equation 2 into the form of the ratio of Rsp divided by R22 yields:

$$Rsp/R22 = (1+TCR*[Tsp-22 \ C]) \quad \text{(Equation 3)}$$

Substituting known (preselected) values into the right side of Equation 2 yields:

$$Rsp/R22 = (1+3320 \ ppm/C*[500 \ C-22 \ C]) = 2.59 \quad \text{(Equation 4)}$$

The pre-selection of a preferred operating temperature of the electrically resistive heating element 48 (e.g., 500 C) combined with the TCR (e.g., 3,320 ppm/C) intrinsically fixed by the electrically resistive thick-film paste selected for the electrically resistive heating element 48 results in a fixed resistance multiplier of 2.59 for the present example. As a consequence, the control circuitry need only incorporate a single signal level multiplier (e.g., 2.59) that then enables a blade 40 having any electrical resistance at room temperature within a nominal range achievable during manufacturing of the blade 40 (e.g., a room temperature resistance in the range from 4.00 to 6.00 ohms) to be elevated to and controlled at the preferred set point temperature (e.g., 500 C) using a fixed resistance multiplier circuit element. Hence, the manufacture of the thick-film printed heating element 48 does not require that its resistance be precisely controlled but rather only maintained within an acceptable range, a requirement easily satisfied using known thick-film printing and firing processes.

The range of the dimensions for the components of the thermal cutting surgical instrument 8, as seen in FIGS. 2 through 7 are summarized below in units of inches:

L1=2.0 to 10.0
L2=0.3 to 0.8
L3=0.4 to 1.0
L4=0.7 to 1.7
L5=0.5 to 2.0
L6=0.75 to 8.0
L7=0.07 to 0.17
L8=0.05 to 0.15
L9=0.20 to 0.40
L10=1.0 to 1.7
L11=4.0 to 8.0
L12=4.0 to 12.0
L13=0.1 to 0.2
L14=36 to 2,400
W1=0.10 to 0.30
W2=0.25 to 0.50
W3=0.015 to 0.050
W4=0.005 to 0.025
W5=0.010 to 0.025
W6=0.007 to 0.020
W7=0.007 to 0.015
W8=0.025 to 0.050
W9=0.010 to 0.030
W10=0.09 to 0.25
W11=0.03 to 0.06
W12=0.15 to 0.30
W13=0.20 to 0.35
W14=0.090 to 0.030
W16=0.025 to 0.050
W17=0.18 to 0.48
W18=0.04 to 0.08
W19=0.010 to 0.025
W20=0.80 to 2.60
W21=1.5 to 3.5
W22=0.020 to 0.035
R1=0.05 to 0.15
t1=0.012 to 0.032
t2=0.002 to 0.005
t3=0.012 to 0.032
t4=0.0005 to 0.0020
t5=0.0005 to 0.0200
t6=0.0005 to 0.0020
t7=0.0005 to 0.0020
t8=0.050 to 0.200
t9=0.030 to 0.150
t10=0.010 to 0.040
t11=0.013 to 0.034

Example

Referring to FIGS. 1, 2 and 3 and by way of example of one preferred design, the dimensions L2, L3, L4, L5, L6, W1, W2, t1, t2 and t11 of blade 40 are 0.340, 0.430, 0.870, 0.530, 0.860, 0.180, 0.350, 0.024, 0.0015 and 0.027 inches, respectively. The core 72 of first substrate 67 in heated portion 42 is silver (minimum 99% silver) and first cladding 70a and second cladding 70b are both stainless steel 430. The support member portion 43 comprises stainless steel 430 throughout. Based on [a] a preselected temperature of 500 C for the electrically resistive heating element 48 for the purposes of incision of tissue and sealing of transected blood vessels during surgery and [b] an assumed duty cycle of 50% (i.e., the fraction of time during surgery procedure that the electrically resistive heating element 48 of blade 40 is at preselected temperature), the total amount of heat that is conducted from the heater portion 42 of blade to handpiece 10 through support member portion 43 is only 0.42 watts. This amount of heat conducted from blade 40 to handpiece 10 can be accommodated by handpiece 10 with increasing the surface temperature above 48 C and, hence, above a temperature that is comfortable for the grasping of handpiece 10 within the gloved hand of the surgeon. Also, based on the above stated dimensions of blade 40 and preselected temperature of 500 C and assuming the application of a maximum power level to the electrically resistive heating element 48 of blade 40 of 40 watts during the heating of the heated portion 42 of blade 40 from 20 C to 500 C, the time required to raise the temperature of heated portion 42 of blade 40 from 20 C to 500 C is only 1.2 seconds. As a result of the brief period required to raise the temperature of heated portion 42 of blade 40 from 20 C to 500 C, the surgeon is able to conveniently energize and de-energize the heated portion 42 of blade 40, as needed during a surgical procedure, without encountering an unacceptable delay for raising the temperature to the temperature required for the purposes of incision of tissue and sealing of transected blood vessels.

Also, based on the above stated dimensions of blade 40 and preselected temperature of 500 C and assuming the application of a maximum power level to the electrically resistive heating element 48 of blade 40 of 20 watts during the incision of tissue and/or the sealing of transected blood vessels, the maximum temperature difference between the electrically resistive heating element 48 and the first substrate 67 as a result of conduction heat transfer through electrically insulative dielectric layer 46 is 12.8 C. The incorporation of a core layer of high thermal conductivity silver in the first substrate serves to maintain the maximum temperature gradient along the length of the heated portion 42 of blade 40 to less than 20 C. As a result, the heated portion 42 of blade 40 that contacts tissue during use is maintained within a narrow range of temperature around a preselected temperature for the electrically resistive heating element (e.g., 500 C). The important benefit of maintaining the heated portion 42 of blade 40 that contacts tissue within a very narrow range of temperature around the preselected temperature is that the surgeon is able to more precisely control both the functions of tissue incision as well as the sealing of transected blood vessels.

The manufacturing process for forming blades according to the preferred embodiment disclosed in connection with FIGS. 2-7 is set forth in the flow chart represented in FIGS. 9A-9D. Those figures should be considered as labeled thereon. Looking to FIG. 9A, the procedure commences with the roll bonding of two materials to form a three-layer laminate as described at block 200. The first of the two materials is silver or copper (e.g., oxygen-free high conductivity or OFHC copper) as represented at block 206 and arrow 208. The second of the two materials is stainless steel (e.g., stainless steel 430) as represented at block 210 and arrow 212.

The roll bonding as represented at block 200 is a process that produces a metallurgical bond as the lattice structures of the metals involved are forced into conformance with each other. Sheets of the stainless steel 430 of equal thickness are positioned on either side of a core sheet of silver or copper with starting thicknesses of all three sheets larger than the finished thickness and in thickness ratios to yield a finished three layer laminate having the preferred finished constituent thicknesses (e.g., 0.003" thick layers of stainless steel 430 roll bonded on both surfaces of a 0.014" thick silver or copper core layer). During the roll bonding process, the high pressure applied produces significant deformation of the three metal layers and causes the sharing of electrons at the interface of the dissimilar metals to produce a bond on the atomic level. No intermediate layers, such as adhesives or brazed metal, are involved. Roll bonding services are provided, for instance, by Engineered Materials Solutions of Attleboro, Mass. The resultant symmetrically laminated cutting portions have been described in FIG. 3 as three-layer laminate comprising core 72, first cladding 70a and second cladding 70b. As represented at arrow 214 and block 216, this laminated three-layer strip is trimmed to a desired width. By way of example and depending upon the blade structure that width will generally be from about 0.9 inch to about 1.2 inch to provide a symmetrical laminate comprising three layers having a total thickness of about 0.014 inch to about 0.032 inch. As noted above and referring to FIG. 3, because of the symmetrical design in terms of materials utilized and thicknesses there is an assurance that while some differential expansion forces will be encountered, they are evenly disposed on either side of the core 72 of high thermal conductivity material thereby avoiding any unwanted warpage of the three layer laminate. By way of example, the core 72 of high thermal conductivity material in three-layer laminate 144 may be silver or copper.

As represented at arrow 218 and block 220 in FIG. 9A and also referring to FIG. 7, blade support member portion 43 incorporating material of low thermal conductivity and appropriate strength is provided. In this regard and by way of example, single metal strips 142a and 142b may be a ferritic stainless steel type 430 as seen in FIG. 7. The single metal strips 142a and 142b for the case of conventional surgical blades may be, for example, between about 2.0 inch and 3.0 inch in width and will have a thickness corresponding with the thickness of the three-layer laminate strip 144. By way of example, an electron beam welding process may be employed to produce this composite three component strip by producing weld lines 44a, 44b along both edges of three-layer laminate strip 144 and adjoining single metal strips 142a and 142b. For example, electron beam welding along the mating edges of metal strips is provided by Bi-Metallix, Inc., East Windsor, Conn.

Next, as represented at arrow 222 and block 224 of FIG. 9B, following the electron beam welding step, the composite three-component strip is cut into lengths that are suitable for electrode-discharge machining. In this regard, as represented at arrow 226 and block 236, stacks of the composite three-component composite three-component sheet 146 in quantities of 20 to 40 sheets are cut within an electro-discharge machine (EDM) to develop the blade blanks as described, for example, at 148a-148l in connection with FIG. 7. The use of EDM machining may preferably be utilized in place of a die cutting process to avoid cracking or damage to the weld zone material. During this EDM cutting procedure, the composite sheets are retained in an oil bath. The result is a quantity of blade blanks that, as represented at arrow 240 and block 242 are cleaned and de-greased to remove residue from the electro-discharge machining process. By way of example, electro-discharge machining services, as described in blocks 236 and 240, are provided by Astro Machine Works, Inc., Ephrata, Pa.

Following such cleaning, as represented at arrow 244 and block 246 of FIG. 9B, each blade blank 148 may optionally be ground along the perimeter of that portion of the heated portion 42 of blade 40 intended to contact tissue during surgical cutting procedures as defined by edge perimeter length, L10 in FIG. 2. The grinding along the tissue contacting edge of the heated portion 42 of blade 40 provides a double-bevel edge as seen in FIG. 3 having a surface contact area preferred for the thermal cutting of tissue. The resulting double-bevel edge produces facets 71a and 71b, as seen in FIG. 3, wherein the included angle of the double-bevel edge is at about 30° to 50°. This relatively large included angle contributes to assured thermal contact with involved tissue. However, the ground edge with double facets is not intended to be surgically sharp since the cutting of tissue is achieved solely by thermal breakdown of the tissue being contacted.

Figure 9C:
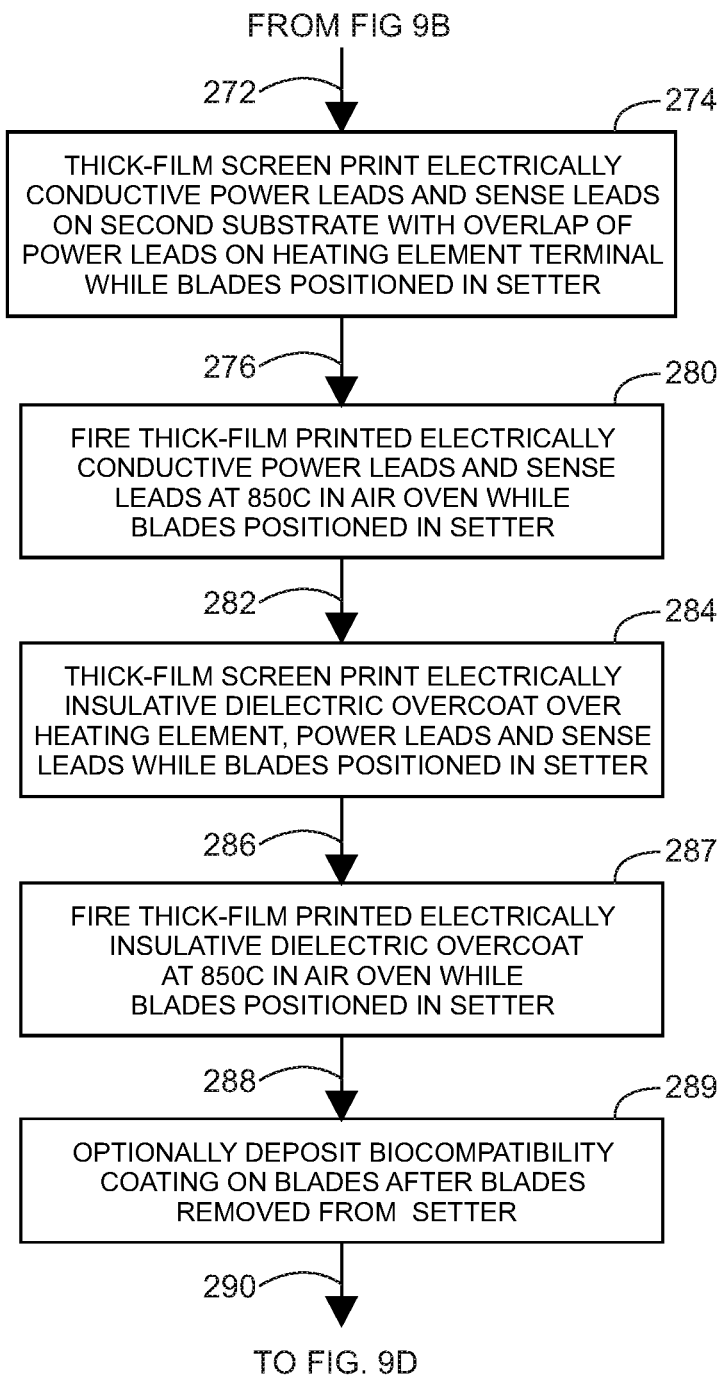

Following the optional grinding along the tissue contacting edge of the heated portion 42 of blade 40, each blade blank 148 is cleaned and degreased and placed in a thick-film printing and firing setter or fixture as represented at arrow 248 and block 250 of FIG. 9C. The setter or fixture is a flat plate of a material capable of withstanding the maximum firing temperature in air, as required for the processing of the thick-film pastes, without loss of the flatness of the setter. The setter contains a multiplicity of accurately machined cavities that match the perimeter of blade blank 148 and hold each the blade blank 148 in positions that register with the images of the thick-film printing patterns incorporated in the screen printing steps. By way of example, the setter may be machined from a plate of stainless steel 430 with an optional post-machining coating of aluminum titanium nitride and containing 12 cavities to receive 12 blade blanks 148 and having overall dimensions of about 6.0 inch wide by about 7.0 inch long to enable their use in conventional screen printing equip Next, as represented at arrow 252 and block 254 of FIG. 9C, the setter supporting a multiplicity of blade blanks 148 is placed in an oven to heat blade blanks 148 to an elevated temperature (e.g., 300 C) in order to pre-oxidize the surface of the blade blanks 148 prior to the application of the electrically insulative dielectric thick film paste.

Next, as represented at arrow 256 and block 258 of FIG. 9C and also referring to FIGS. 2 through 6A, the setter supporting a multiplicity of pre-oxidized blade blanks 148 is positioned in a screen-printing apparatus and an electrically insulative dielectric layer 46 is screen printed on first surface 69 of first substrate 67 and first surface 75 of second substrate 80. Next, as represented at arrow 260 and block 262, the setter supporting a multiplicity of blade blanks 148 with screen-printed electrically insulative dielectric layer 46 on the first surface 69 of first substrate 67 and the first surface 75 of second substrate 80 is placed in an oven and heated to an elevated temperature in air or an alternative non-oxidizing atmosphere to "fire" the thick-film paste (e.g., heating setter containing a multiplicity of thick-film printed blade blanks 148 to a temperature of 850 C in air). The selection of the atmosphere in the oven during the firing process will depend on the recommendations provided by the thick-film paste supplier.

Next, as represented at arrow 264 and block 266 of FIG. 9C and also referring to FIGS. 2 through 6A, the setter supporting a multiplicity of blade blanks 148 is returned to screen printing apparatus and an electrically resistive heating element is screen-printed on first substrate 67 of blade 40 over surface of previously screen printed and fired electrically insulative dielectric layer 46. Next, as represented at arrow 268 and block 270, the setter supporting a multiplicity of blade blanks 148 with screen-printed electrically resistive heating element disposed on first substrate 69 of blade blank 148 is placed in an oven and heated to an elevated temperature in air or an alternative non-oxidizing atmosphere to "fire" the thick-film paste (e.g., heating setter containing a multiplicity of thick-film printed blade blanks 148 to a temperature of 850 C in air).

Next, as represented at arrow 272 and block 274 of FIG. 9D and also referring to FIGS. 2 through 6A, the setter supporting a multiplicity of blade blanks 148 is returned to screen printing apparatus and electrically conductive power leads 52a, 52b and electrically conductive sense leads 54a, 54b are screen-printed on second substrate 80 of blade 40 over surface of previously screen printed and fired electrically insulative dielectric layer 46. As seen in FIGS. 2 and 2A, the electrically conductive power leads 52a, 52b and electrically conductive sense leads 54a, 54b are screen-printed in such a manner that they overlap and are in electrical communication with terminals 47a, 47b of electrically resistive heating element 48. Next, as represented at arrow 276 and block 280, the setter supporting a multiplicity of blade blanks 148 with screen-printed electrically conductive power leads 52a, 52b and electrically conductive sense leads 54a, 54b is placed in an oven and heated to an elevated temperature in air or an alternative non-oxidizing atmosphere to "fire" the thick-film paste (e.g., heating setter containing a multiplicity of thick-film printed blade blanks 148 to a temperature of 850 C in air).

Next, as represented at arrow 282 and block 284 of FIG. 9D and also referring to FIGS. 2 through 6A, the setter supporting a multiplicity of blade blanks 148 is returned to screen printing apparatus and electrically insulative dielectric overcoat 74 is screen-printed over surfaces of previously screen printed and fired electrically resistive heating element 48 as well as the distal portions of electrically conductive power leads 52a, 52b and electrically conductive sense leads 54a, 54b as seen in FIGS. 2 and 2B. A length, L9, at the proximal end of electrically conductive power leads 52a, 52b and electrically conductive sense leads 54a, 54b is not covered with electrically insulative dielectric overcoat 74 to enable electrical communication between electrical contacts within the handpiece 10 (not shown) and the proximal ends of the thick-film printed and fired electrically conductive power leads 52a, 52b and electrically conductive sense leads 54a, 54b. Next, as represented at arrow 286 and block 287, the setter supporting a multiplicity of blade blanks 148 with screen-printed electrically insulative dielectric overcoat 74 is placed in an oven and heated to an elevated temperature in air or an alternative non-oxidizing atmosphere to "fire" the thick-film paste (e.g., heating setter containing a multiplicity of thick-film printed blade blanks 148 to a temperature of 850 C in air).

Next, as represented at arrow 288 and block 289 of FIG. 9D and also referring to FIGS. 2 through 6A, blade blanks 148 now incorporate thick-film printed and fired electrically insulative dielectric layer 46 followed by thick-film printed and fired electrically resistive heating element 48, electrically conductive power leads 52a, 52b as well as electrically conductive sense leads 54a, 54b and, finally, thick-film printed and fired electrically insulative dielectric overcoat 74. The blade blanks 148 having the above specified thick-film printed and fired layers are next removed from the setter. Depending on material selected for the core 72 of the heated portion of the blade 40, a biocompatible coating 82 is optionally deposited on those distal portions of blade 40 that may come in physical contact with human tissue or blood. By way of example and referring to FIGS. 2-6A, if [a] first substrate 67 of blade 40 comprises a laminate structure incorporating a core 72 of high thermal conductivity copper with first and second claddings 70a, 70b of stainless steel 430 and [b] second substrate is stainless steel 430, then a biocompatible coating will be required due to the exposed surfaces of copper along the edges of first substrate 67 as seen in FIG. 3. As stated earlier, copper and its alloys are known to exhibit a high level of cytotoxicity with respect to the cells of human tissue and blood. By way of example, a thin coating of titanium nitride having a thickness of 1 to 5 microns may be applied to blade 40 up to and distal to the proximal edge of electrically insulative dielectric overcoat 74 as seen in FIG. 2B. The biocompatible coating 82 of titanium nitride may be further sealed to assure a complete barrier coating. By way of example, such a titanium nitride biocompatible coating 82 can be applied by Dayton Coating Technologies, Dayton, Ohio.

By way of another example and referring to FIGS. 2-6A, if [a] first substrate 67 of blade 40 comprises a laminate structure incorporating a core 72 of high thermal conductivity silver combined with first and second claddings 70a, 70b of stainless steel 430 and [b] second substrate is stainless steel 430, then no additional biocompatibility coating 82 is necessary. In this preferred embodiment, no additional biocompatibility coating 82 is required since all components of blade 40, including the glass-based electrically insulative dielectric overcoat 74, that contact tissue or blood during surgical use are known to be biocompatible materials.

As represented at arrow 290 and block 292 in FIG. 9E, the electrical resistance of the electrically resistive heating element 48 disposed on blade 40 is tested using a handpiece incorporating electrical contacts that enable electrical communication with electrically conductive power leads 52a, 52b and electrically conductive sense leads 54a, 54b. That electrical resistance of the electrically resistive heating element 48, for example, should be in a range from 4.0 ohms to 6.0 ohms at room temperature (e.g., 22 C). Accordingly, electrical resistance values outside this range will represent either an open circuit or short circuit condition. Under those conditions, such blades 40 are rejected with 100% of the blades 40 being subjected to this electrical resistance test. Accordingly, as represented at arrow 294 and block 296, a query is made as to whether the electrical resistance of the electrically resistive heating element 48 disposed on blade 40 is within the specified range of acceptable electrical resistance values. Where it is not, then as represented by arrow 298 and block 300, blade 40 is rejected. On the other hand, where blade 40 passes this electrical resistance test, then as represented at arrow 302 and block 304, a power application test is carried out to check for the capability of the electrically resistive heating element 48 disposed on blade 40 to withstand the maximum applicable power level during use. In this regard, the portions of the thick-film printed and fired electrically resistive heating element 48 disposed on blade 40 may exhibit a thinned out or narrowed portion or a partially cracked portion. Under a ramping-up power application such defects will cause the electrically resistive heating element 48 to fail as determined by the measured electrical resistance of the blade that must be within a preselected range when power is applied to the electrically resistive heating element 48. By way of example, owing to the positive temperature coefficient of resistance of the electrically resistive heating element 48, the acceptable resistance range while power is applied to the electrically resistive heating element 48 may be 9.0 to 17.0 ohms corresponding an acceptable electric resistance range of 4.0 to 6.0 ohms at room temperature and a temperature coefficient resistance multiplier of 2.6. Accordingly, 100% of the blades must pass this power-application test. As represented at arrow 306 and block 308, a query is made as to whether a given blade 40 has passed the power-up test. In the event that it has not, then as represented at arrow 310 and block 312, blade 40 is rejected. Where the power-up test is passed, then, as represented at arrow 314 and block 316, sterilization and packaging procedures are undertaken. Sterilization may be, for example, by either gamma radiation impingement or ethylene oxide envelopment. Following packaging, as represented at arrow 318 and block 320, the packaged and sterilized blades 40 are placed in finished goods inventory and, as represented at arrow 322 and block 324, ultimately the packaged blades 40 are shipped to a customer.

All terms not specifically defined herein are considered to be defined according to Dorland's Medical Dictionary, and if not defined therein according to Webster's New Twentieth Century Dictionary Unabridged, Second Edition.

While the apparatus, system, and method have been described with reference to various embodiments, those skilled in the art will understand that various changes may be made and equivalents may be substituted for elements thereof without departing from the scope and essence of the disclosure. In addition, many modifications may be made to adapt a particular situation or material in accordance with the teachings of the disclosure without departing from the essential scope thereof. Therefore, it is intended that the disclosure not be limited to the particular embodiments disclosed, but that the disclosure will include all embodiments falling within the scope of the appended claims.

I claim:

1. A thermal cutting surgical instrument (8) having a blade (40) operable at a resistance-feedback controlled, preselected set point temperature for incising tissue without a mechanically sharp cutting edge and for sealing transected blood vessels, the thermal cutting surgical instrument comprising:

a handpiece (10) supporting the blade (40) that includes a support member, the handpiece incorporating a heating element temperature control circuitry (30), a user control switch (22), a plurality of lights (24, 26, 28) providing visual cues to indicate the state of operation of the thermal cutting surgical instrument, and a cable (60) integral with the handpiece, the cable having a plug (62) removably attachable to a receptacle (61) of a direct current (DC) power supply (64), said heating element temperature control circuitry (30) having a fixed resistance multiplier circuit element for determining the preselected set point temperature;

the blade having a heated portion (42) and a support portion (43), wherein
  the heated portion including a first substrate (67) that includes a core (72) of high thermal conductivity silver and that includes a first surface;
  the support portion including a second substrate (80) of low thermal conductivity stainless steel and that includes a first surface,
wherein the first substrate is joined to the second substrate;

an electrically insulative dielectric layer (46) disposed on the first surface of the first substrate and on the first surface of second substrate of low thermal conductivity stainless steel;

an electrically resistive heating element (48) disposed on the electrically insulative dielectric layer in the heated portion of the blade;

electrically conductive power leads (52a, 52b) and electrically conductive sense leads (54a, 54b) disposed on the electrically insulative dielectric layer disposed on the second substrate in the support portion of the blade and that are in electrical communication with the electrically resistive heating element, the electrically conductive power leads and the electrically conductive sense leads each having a distal portion;

an electrically insulative dielectric overcoat (74) layer disposed on the electrically resistive heating element and on the distal portion of the electrically conductive power leads and the electrically conductive sense leads;

wherein the electrically insulative dielectric layer, the electrically resistive heating element, the electrically conductive power leads, the electrically conductive sense leads and the electrically insulative dielectric overcoat layer can be moved repeatedly between air, tissue, blood, or other liquid without fracturing while the electrically resistive heating element is at a resistance-feedback controlled, preselected set point temperature.

2. The thermal cutting surgical instrument (8) of claim 1, wherein the electrically insulative dielectric layer (46), the electrically resistive heating element (48) and the electrically insulative dielectric overcoat (74) layer have a combined thickness of between about 0.0015 and 0.0100 inch.

3. The thermal cutting surgical instrument (8) of claim 1, wherein the electrically insulative dielectric layer (46), the electrically conductive power leads (52a, 52b) or the electrically conductive sense leads (54a, 54b) and the electrically insulative dielectric overcoat (74) layer have a combined thickness of between about 0.0015 and 0.0100 inch.

4. The thermal cutting surgical instrument (8) of claim 1, wherein the blade (40) in the heated portion and the support member portion have a thickness of between about 0.013 and 0.034 inch.

5. The thermal cutting surgical instrument (8) of claim 1, wherein the heated portion of the blade (40) has a width of between about 0.10 and 0.30 inch.

6. The thermal cutting surgical instrument (8) of claim 1, wherein a source of substantially constant DC voltage is provided to the handpiece (10) by the direct current (DC) power supply (64) removably connectable to a wall outlet (66).

7. The thermal cutting surgical instrument (8) of claim 1, wherein a source of substantially constant DC voltage is provided by a battery located within the handpiece (10).

8. The thermal cutting surgical instrument (8) of claim 1, wherein the heated portion of the blade is a three-layer laminate comprising a core (72) of high thermal conductivity silver having opposite lateral faces, said opposite lateral faces having claddings (70a, 70b) of low thermal conductivity stainless steel on each of the opposite lateral faces of the core (72) of high thermal conductivity silver.

9. The thermal cutting surgical instrument of claim 8, wherein the claddings (70a, 70b) of low thermal conductivity stainless steel is austenitic or ferritic stainless steel.

10. The thermal cutting surgical instrument (8) of claim 1, wherein a biocompatible material is disposed on the heated portion and the support portion (43) of blade (40).

11. The thermal cutting surgical instrument system of claim 10, wherein the biocompatible material is titanium nitride or aluminum titanium nitride.

12. The thermal cutting surgical instrument (8) of claim 1, wherein the electrically insulative dielectric layer (46), the electrically resistive heating element (48), the electrically conductive power leads (52a, 52b) the electrically conductive sense leads (54a, 54b), and the electrically insulative dielectric overcoat (74) layer are screen-printable thick-film materials that are fired at temperatures in the range from 600 C to 900 C.

13. The thermal cutting surgical instrument (8) of claim 1, wherein the heated portion (42) of the blade (40) incorporates a core (72) of high thermal conductivity silver having a thermal conductivity of at least 3 watts/cm-C.

14. The thermal cutting surgical instrument (8) of claim 1, wherein the second substrate (80) of low thermal conductivity stainless steel in the support portion (43) of the blade (40) has a thermal conductivity of less than 0.6 watts/cm-C.

15. The thermal cutting surgical instrument (8) of claim 1, wherein the heated portion (42) of the blade (40) has a heat capacity of less than 0.025 calories/C.

16. The thermal cutting surgical instrument of claim 1, wherein the preselected set point temperature of the electrically resistive heating element during use is a value selected from within the range from 400 to 600 C.

17. The thermal cutting surgical instrument of claim 1, wherein the preselected set point temperature of the electrically resistive heating element (48) during use is 500 C.

18. A method for making a thermal cutting surgical instrument (8) operable at a resistance-feedback controlled, preselected set point temperature for incising tissue without a mechanically sharp cutting edge and for sealing transected blood vessels, comprising the steps of:
providing a handpiece (10) incorporating a heating element temperature control circuitry (10), a user control switch (22), a plurality of lights (24,26,28) as visual cues to indicate the state of operation of the thermal cutting surgical instrument (8) to an operator and a cable (60) integral with the handpiece (10) and removably attachable to a receptacle (61) of a direct current (DC) power supply (64) connected to a wall outlet (66), said direct current (DC) power supply providing a source of substantially constant DC voltage;
providing a blade (40) supported by the handpiece (10), the blade (40) having a heated portion (42) and a support portion (43), said heated portion of the blade is a first substrate (67) having a core (72) of high thermal conductivity silver and having opposite lateral faces, said opposite lateral faces having claddings (70a, 70b) of low thermal conductivity stainless steel on each of the opposite lateral faces of the core (72) of high thermal conductivity silver;
joining the first substrate (67), having a core (72) of high thermal conductivity silver to a second substrate (80) of low thermal conductivity stainless steel in the support portion (43) of the blade, the first substrate (67) incorporating a core (72) of high thermal conductivity silver having a first surface (69) and second substrate (43) of low thermal conductivity stainless steel having a first surface (75);
disposing the electrically insulative dielectric layer (46) on the first surface (69) of the first substrate (67) incorporating a core (72) of high thermal conductivity silver and disposing an electrically insulative dielectric layer (46) on the first surface (75) of second substrate (80) of low thermal conductivity stainless steel;
disposing an electrically resistive heating element (48) on the electrically insulative dielectric layer (46) disposed on the first substrate (67) incorporating a core (72) of high thermal conductivity silver;
disposing electrically conductive power leads (52a, 52b) and electrically conductive sense leads (54a, 54b) on the electrically insulative dielectric layer (46) disposed on the second substrate (80) of low thermal conductivity stainless steel in the support portion (43) of the blade (40), said electrically conductive power leads and the electrically conductive sense leads in electrical communication with the electrically resistive heating element (48), the electrically conductive power leads (52a, 52b) and the electrically conductive sense leads (54a, 54b), each having a distal portion;
disposing an electrically insulative dielectric overcoat (74) layer on the electrically resistive heating element (48) disposed on the first substrate (67) incorporating a core (72) of high thermal conductivity silver and on the distal portion of the electrically conductive power leads (52a, 52b) and the electrically conductive sense leads (54a, 54b) disposed on the second substrate (80),
wherein the electrically insulative dielectric layer (46), the electrically resistive heating element (48), the electrically conductive power leads (52a,52b) and the electrically conductive sense leads (54a,54b), and the electrically insulative dielectric overcoat (74) layer can be moved repeatedly between air, tissue, blood, or other liquid without fracturing while the electrically resistive heating element is at a resistance-feedback controlled, preselected set point temperature.

19. The method of claim 18, wherein the combined thickness of the electrically insulative dielectric layer, the electrically insulative dielectric overcoat layer and the electrically resistive heating element or the electrically conductive power leads or electrically the conductive sense leads is 0.0015 to 0.010 inch.

20. The method of claim 18, wherein the thickness of the blade in the heated portion and the support member portion is 0.012 to 0.032 inch.

21. The method of claim 18, wherein the width of the heated portion of blade is 0.10 to 0.30 inch.

22. The method of claim 18, wherein a source of substantially constant DC voltage is provided by a battery located within the handpiece (10).

23. The method of claim 18, wherein the material for the claddings (70*a*, 70*b*) is austenitic or ferritic stainless steel.

24. The method of claim 18, wherein a coating of biocompatible material is disposed on the surface of the heated portion (42) and the support portion (43) blade (40).

25. The method of claim 24, wherein the biocompatible material is titanium nitride or aluminum titanium nitride.

26. The method of claim 18, wherein the electrically insulative dielectric layer (46), the electrically resistive heating element (48), the electrically conductive power leads (52*a*, 52*b*), the electrically conductive sense leads (54*a*, 54*b*) and the electrically insulative dielectric overcoat (74) layer are screen-printable thick-film materials that are fired at temperatures in the range from 600 C to 900 C.

27. The method of claim 18, wherein the thermal conductivity of the core (72) of the first substrate (67) is at least 3 watts/cm-C.

28. The method of claim 18, wherein the thermal conductivity of the second substrate (80) is less than 0.6 watts/cm-C.

29. A method for making the blade (40) of claim 1 comprising the steps of:
  [a] forming a first slot having a width W20 and a depth t9 at a center of a first stainless steel strip (160*a*) having a thickness of t8 and a width W21+W20+W21 by abrasive grinding or skiving;
  [b] placing a first metal inlay strip (166*a*) of high thermal conductivity silver having a width slightly less than any part of the range of values of the slot width W20 and a thickness t9 within a slot in the first stainless steel strip to form a first composite strip;
  [c] roll bonding the first composite strip of Step [b] comprising a first stainless steel strip and a first metal inlay strip, the first composite strip having a length ranging from several feet to 100 feet or more;
  [d] forming a second slot having a width W20 and a depth t9 at a center of a second stainless steel strip (160*b*) having a thickness of t8 and a also the same Step [a] width of W21+W20+W21 by abrasive grinding or skiving;
  [e] placing a second metal inlay strip (166*b*) of high thermal conductivity silver having a width slightly less than any part of the range of values of the slot width W20 and a thickness t9 within a slot in second stainless steel strip to form a second composite strip;
  [f] roll bonding the second composite strip of Step [e] comprising a second stainless steel strip and a second metal inlay strip, the second composite strip having a length L4 ranging from several feet to 100 feet or more;
  [g] positioning and aligning the first and the second roll bonded composite strips such that the first and the second metal inlay strips (166*a*, 166*b*) face each other;
  [h] roll bonding a first composite strip and a second composite strips (166*a*, 166*b*) together providing a metallurgical bond between the first and the second composite strips to form a two-component strip having a core layer of thermally conductive metal inlay strips in the center of the two-component strip having a length L4;
  [i] dividing the two-component strip of Step [h] into lengths L12 to form a two-component sheet (170);
  [j] perforating the two-component sheet using electro-discharge machining to form a individual blade blanks (148) having a thermally conductive portion with a length L3 and a width W1 and;
  [k] separating the individual blade blanks having a length L1 from the two-component sheet and placing on a custom-designed setter that precisely positions and holds each of the individual blade blanks in a preselected position within an array wherein the same side of each blade blank is facing up, and
  [l] sequentially thick-film print and fire an electrically insulative dielectric layer on the heated portion of the blade and the support portion of the blade, an electrically resistive heating element on the heated portion of the blade, the electrically conductive power leads and the sense leads on the support portion of the blade and extending to the heated portion of the blade to provide electrical communication between the power leads and the heating element and, lastly, an electrically insulative dielectric overcoat disposed over the heating element and the distal portion of the power leads and the sense leads.

* * * * *